(12) United States Patent
Backus et al.

(10) Patent No.: US 10,201,416 B2
(45) Date of Patent: Feb. 12, 2019

(54) REPLACEMENT HEART VALVE IMPLANT WITH INVERTIBLE LEAFLETS

(71) Applicant: BOSTON SCIENTIFIC SCIMED, INC., Maple Grove, MN (US)

(72) Inventors: Andrew J. H. Backus, Santa Cruz, CA (US); Michael P. Calomeni, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/466,005

(22) Filed: Mar. 22, 2017

(65) Prior Publication Data
US 2017/0325938 A1    Nov. 16, 2017

Related U.S. Application Data

(60) Provisional application No. 62/336,944, filed on May 16, 2016.

(51) Int. Cl.
*A61F 2/24* (2006.01)
*A61F 2/90* (2013.01)

(52) U.S. Cl.
CPC ............ *A61F 2/2403* (2013.01); *A61F 2/243* (2013.01); *A61F 2/2418* (2013.01);
(Continued)

(58) Field of Classification Search
CPC ........ A61F 2/24; A61F 2/2418; A61F 2/2427; A61F 2/243; A61F 2/2439;
(Continued)

(56) References Cited

U.S. PATENT DOCUMENTS

| 15,192 A | 6/1856 | Peale |
|---|---|---|
| 2,682,057 A | 6/1954 | Lord |

(Continued)

FOREIGN PATENT DOCUMENTS

| AU | 2002329324 B2 | 7/2007 |
|---|---|---|
| CN | 1338951 A | 3/2002 |

(Continued)

OTHER PUBLICATIONS

US 8,062,356, 11/2011, Salahieh et al. (withdrawn)
(Continued)

*Primary Examiner* — Alvin Stewart
(74) *Attorney, Agent, or Firm* — Seager, Tufte & Wickhem LLP

(57) ABSTRACT

A locking mechanism for a medical implant may include a buckle member, a post member axially translatable with respect to the buckle member, the post member including a receiving portion proximate a proximal end of the post member, a distal end, a laterally-arched central body portion extending between the receiving portion and the distal end, and a cantilevered leg extending proximally from the distal end, and an actuator element including a proximal shaft portion and a distal engagement portion, the distal engagement portion being configured to releasably engage the receiving portion of the post member. The proximal shaft portion may be pivotable with respect to the distal engagement portion.

20 Claims, 13 Drawing Sheets

(52) U.S. Cl.
CPC .......... *A61F 2/2436* (2013.01); *A61F 2/2439* (2013.01); *A61F 2/90* (2013.01); *A61F 2220/005* (2013.01); *A61F 2220/0008* (2013.01); *A61F 2220/0033* (2013.01); *A61F 2220/0075* (2013.01); *A61F 2230/0013* (2013.01)

(58) Field of Classification Search
CPC ................ A61F 2002/9505; A61F 2/95; A61F 2002/9511; A61M 2025/024; A61M 25/04; A61M 29/00
See application file for complete search history.

(56) References Cited

U.S. PATENT DOCUMENTS

| | | |
|---|---|---|
| 2,701,559 A | 2/1955 | Cooper |
| 2,832,078 A | 4/1958 | Williams |
| 3,029,819 A | 4/1962 | Starks |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,221,006 A | 11/1965 | Moore et al. |
| 3,334,629 A | 5/1967 | Cohn |
| 3,365,728 A | 1/1968 | Edwards et al. |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |

(56) References Cited

U.S. PATENT DOCUMENTS

| | | |
|---|---|---|
| 5,411,552 A | 5/1995 | Andersen et al. |
| 5,425,739 A | 6/1995 | Jessen |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,469,868 A | 11/1995 | Reger |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,489,297 A | 2/1996 | Duran |
| 5,500,014 A | 3/1996 | Quijano et al. |
| 5,507,767 A | 4/1996 | Maeda et al. |
| 5,522,881 A | 6/1996 | Lentz |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,784 A | 5/1997 | Strecker |
| 5,645,559 A | 7/1997 | Hachtman et al. |
| 5,653,745 A | 8/1997 | Trescony et al. |
| 5,662,671 A | 9/1997 | Barbut et al. |
| 5,667,523 A | 9/1997 | Bynon et al. |
| 5,674,277 A | 10/1997 | Freitag |
| 5,681,345 A | 10/1997 | Euteneuer |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,772,609 A | 6/1998 | Nguyen et al. |
| 5,776,188 A | 7/1998 | Shepherd et al. |
| 5,782,904 A | 7/1998 | White et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,015,431 A | 1/2000 | Thornton et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,110,198 A | 8/2000 | Fogarty et al. |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,911 B1 | 3/2001 | Milo |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,309,417 B1 | 10/2001 | Spence et al. |

(56) References Cited

U.S. PATENT DOCUMENTS

| | | |
|---|---|---|
| 6,312,465 B1 | 11/2001 | Griffin et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,387,122 B1 | 5/2002 | Cragg |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,540,782 B1 | 4/2003 | Snyders |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,729,356 B1 | 5/2004 | Baker et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,773,456 B1 | 8/2004 | Gordon et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,814,754 B2 | 11/2004 | Greenhalgh |
| 6,821,297 B2 | 11/2004 | Snyders |
| 6,824,041 B2 | 11/2004 | Grieder et al. |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |

(56) References Cited

U.S. PATENT DOCUMENTS

| | | |
|---|---|---|
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |
| 7,147,663 B1 | 12/2006 | Berg et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,473,417 B2 | 1/2009 | Zeltinger et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,601,159 B2 | 10/2009 | Ewers et al. |
| 7,622,276 B2 | 11/2009 | Cunanan et al. |
| 7,628,802 B2 | 12/2009 | White et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,914,574 B2 | 3/2011 | Schmid et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,287,584 B2 | 10/2012 | Salahieh et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,348,999 B2 | 1/2013 | Kheradvar et al. |
| 8,366,767 B2 | 2/2013 | Zhang |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,512,394 B2 | 8/2013 | Schmid et al. |
| 8,523,936 B2 | 9/2013 | Schmid et al. |
| 8,540,762 B2 | 9/2013 | Schmid et al. |
| 8,545,547 B2 | 10/2013 | Schmid et al. |
| 8,579,962 B2 | 11/2013 | Salahieh et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,696,743 B2 | 4/2014 | Holecek et al. |
| 8,795,354 B2 | 8/2014 | Benichou et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 9,168,131 B2 | 10/2015 | Yohanan et al. |
| 9,283,072 B2 | 3/2016 | Bruchman et al. |
| 9,393,114 B2 * | 7/2016 | Sutton ............... A61F 2/2436 |
| 9,901,445 B2 * | 2/2018 | Backus ............... A61F 2/2412 |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0027338 A1 | 10/2001 | Greenberg |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055774 A1 | 5/2002 | Liddicoat |
| 2002/0058987 A1 | 5/2002 | Butaric et al. |

(56) References Cited

U.S. PATENT DOCUMENTS

| | | |
|---|---|---|
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0156522 A1 | 10/2002 | Ivancev et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0074058 A1 | 4/2003 | Sherry |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0165352 A1 | 9/2003 | Ibrahim et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204249 A1 | 10/2003 | Letort |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2003/0236567 A1 | 12/2003 | Elliot |
| 2004/0019374 A1 | 1/2004 | Hojeibane et al. |
| 2004/0033364 A1 | 2/2004 | Spiridigliozzi et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |

(56) References Cited

U.S. PATENT DOCUMENTS

| | | |
|---|---|---|
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025857 A1 | 2/2006 | Bergheim et al. |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0088431 A1 | 4/2007 | Bourang et al. |
| 2007/0100427 A1 | 5/2007 | Perouse |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0096598 A1 | 4/2009 | Tengler et al. |
| 2009/0171456 A1 | 7/2009 | Kveen et al. |
| 2009/0216312 A1 | 8/2009 | Straubinger et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0036479 A1 | 2/2010 | Hill et al. |
| 2010/0049313 A1 | 2/2010 | Alon et al. |
| 2010/0082089 A1 | 4/2010 | Quadri et al. |
| 2010/0094399 A1 | 4/2010 | Dorn et al. |
| 2010/0121434 A1 | 5/2010 | Paul et al. |
| 2010/0161045 A1 | 6/2010 | Righini |
| 2010/0185275 A1 | 7/2010 | Richter et al. |
| 2010/0191320 A1 | 7/2010 | Straubinger et al. |
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0268332 A1 | 10/2010 | Tuval et al. |
| 2010/0280495 A1 | 11/2010 | Paul et al. |
| 2010/0298931 A1 | 11/2010 | Quadri et al. |
| 2011/0040366 A1 | 2/2011 | Goetz et al. |
| 2011/0098805 A1 | 4/2011 | Dwork et al. |
| 2011/0218619 A1 | 9/2011 | Benichou et al. |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264203 A1 | 10/2011 | Dwork et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |

(56) References Cited

U.S. PATENT DOCUMENTS

| | | | |
|---|---|---|---|
| 2012/0179244 A1 | 7/2012 | Schankereli et al. | |
| 2012/0197379 A1 | 8/2012 | Laske et al. | |
| 2012/0303113 A1 | 11/2012 | Benichou et al. | |
| 2012/0303116 A1 | 11/2012 | Gorman et al. | |
| 2012/0330409 A1 | 12/2012 | Haug et al. | |
| 2013/0013057 A1 | 1/2013 | Salahieh et al. | |
| 2013/0018457 A1 | 1/2013 | Gregg et al. | |
| 2013/0030520 A1 | 1/2013 | Lee et al. | |
| 2013/0079867 A1 | 3/2013 | Hoffman et al. | |
| 2013/0079869 A1 | 3/2013 | Straubinger et al. | |
| 2013/0096664 A1 | 4/2013 | Goetz et al. | |
| 2013/0123796 A1 | 5/2013 | Sutton et al. | |
| 2013/0138207 A1 | 5/2013 | Quadri et al. | |
| 2013/0158656 A1 | 6/2013 | Sutton et al. | |
| 2013/0166017 A1 | 6/2013 | Cartledge et al. | |
| 2013/0184813 A1 | 7/2013 | Quadri et al. | |
| 2013/0190865 A1 | 7/2013 | Anderson | |
| 2013/0204360 A1 | 8/2013 | Gainor | |
| 2013/0253640 A1 | 9/2013 | Meiri et al. | |
| 2013/0289698 A1 | 10/2013 | Wang et al. | |
| 2013/0296999 A1 | 11/2013 | Burriesci et al. | |
| 2013/0304199 A1 | 11/2013 | Sutton et al. | |
| 2013/0310917 A1 | 11/2013 | Richter et al. | |
| 2013/0310923 A1 | 11/2013 | Kheradvar et al. | |
| 2014/0018911 A1 | 1/2014 | Zhou et al. | |
| 2014/0031924 A1 | 1/2014 | Bruchman et al. | |
| 2014/0094904 A1 | 4/2014 | Salahieh et al. | |
| 2014/0114340 A1* | 4/2014 | Zhou | A61F 2/0077 606/198 |
| 2014/0114405 A1 | 4/2014 | Paul et al. | |
| 2014/0114406 A1 | 4/2014 | Salahieh et al. | |
| 2014/0121766 A1 | 5/2014 | Salahieh et al. | |
| 2014/0135912 A1 | 5/2014 | Salahieh et al. | |
| 2014/0243967 A1 | 8/2014 | Salahieh et al. | |
| 2014/0324160 A1 | 10/2014 | Benichou et al. | |
| 2015/0012085 A1 | 1/2015 | Salahieh et al. | |
| 2015/0073540 A1 | 3/2015 | Salahieh et al. | |
| 2015/0073541 A1 | 3/2015 | Salahieh et al. | |
| 2015/0127094 A1 | 5/2015 | Salahieh et al. | |
| 2015/0245909 A1 | 9/2015 | Salahieh et al. | |
| 2016/0045307 A1 | 2/2016 | Yohanan et al. | |
| 2016/0143731 A1* | 5/2016 | Backus | A61F 2/2412 623/2.17 |
| 2016/0157998 A1 | 6/2016 | Bruchman et al. | |
| 2016/0199184 A1 | 7/2016 | Ma et al. | |
| 2016/0213467 A1* | 7/2016 | Backus | A61F 2/2418 |
| 2016/0220359 A1* | 8/2016 | Backus | A61F 2/2409 |
| 2016/0220360 A1* | 8/2016 | Lin | A61F 2/2409 |
| 2016/0256271 A1* | 9/2016 | Backus | A61F 2/2418 |
| 2016/0296322 A1* | 10/2016 | Edelman | A61F 2/2412 |
| 2017/0042669 A1* | 2/2017 | Backus | A61F 2/2418 |
| 2017/0042671 A1* | 2/2017 | Backus | A61F 2/2418 |
| 2017/0042672 A1* | 2/2017 | Backus | A61F 2/2418 |
| 2017/0042676 A1* | 2/2017 | Backus | A61F 2/2445 |
| 2017/0071729 A1* | 3/2017 | Wrobel | A61F 2/2415 |
| 2017/0304049 A1* | 10/2017 | Hayes | A61F 2/2409 |
| 2017/0319335 A1* | 11/2017 | Backus | A61F 2/2412 |
| 2017/0325928 A1* | 11/2017 | Ino | A61F 2/0095 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 579523 A1 | 1/1994 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1690515 A1 | 8/2006 |
| EP | 1605871 B1 | 7/2008 |
| EP | 2047824 B1 | 5/2012 |
| EP | 2749254 B1 | 6/2015 |
| EP | 2926766 A1 | 10/2015 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A2 | 9/1999 |
| WO | 9951165 A1 | 10/1999 |
| WO | 0009059 A2 | 2/2000 |
| WO | 2000009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106959 A1 | 2/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 2001054625 A1 | 8/2001 |

(56) References Cited

FOREIGN PATENT DOCUMENTS

| | | |
|---|---|---|
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03032869 A1 | 4/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03015851 B1 | 11/2003 |
| WO | 03094793 A1 | 11/2003 |
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006093795 A1 | 9/2006 |
| WO | 2006138391 A2 | 12/2006 |
| WO | 2007009117 A1 | 1/2007 |
| WO | 2007033093 A2 | 3/2007 |
| WO | 2007035471 A2 | 3/2007 |
| WO | 2005102015 A3 | 4/2007 |
| WO | 2007044285 A2 | 4/2007 |
| WO | 2007053243 A2 | 4/2007 |
| WO | 2007058847 A2 | 5/2007 |
| WO | 2007092354 A2 | 8/2007 |
| WO | 2007097983 A2 | 8/2007 |
| WO | 2008028569 A1 | 3/2008 |
| WO | 2008035337 A2 | 3/2008 |
| WO | 2010042950 A2 | 4/2010 |
| WO | 2010098857 A1 | 9/2010 |
| WO | 2012116368 A2 | 8/2012 |
| WO | 2012162228 A1 | 11/2012 |
| WO | 2013009975 A1 | 1/2013 |
| WO | 2013028387 A2 | 2/2013 |
| WO | 2013074671 A1 | 5/2013 |
| WO | 2013096545 A1 | 6/2013 |
| WO | 2016126511 A2 | 8/2016 |

OTHER PUBLICATIONS

US 8,062,357, 11/2011, Salahieh et al. (withdrawn)
US 8,075,614, 12/2011, Salahieh et al. (withdrawn)
US 8,133,271, 03/2012, Salahieh et al. (withdrawn)
US 8,211,170, 07/2012, Paul et al. (withdrawn)
International Search Report and Written Opinion dated Jul. 28, 2017 for International Application No. PCT/US2017/032284.
U.S. Appl. No. 60/553,945 to White, filed March 18, 2004.
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EP Patent Office, EP Application No. 04813777.2, dated Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in the aorta and the beating heart of closed chest pigs (Abstract)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report MIME 1501-1502. Technical Design Report Northeastern University, pp. 1-93, Nov. 5, 2007.
Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent—Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation. New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.

(56) References Cited

OTHER PUBLICATIONS

Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg., 125(3):741-743, Mar. 2003.
Boudjemline et al., "Steps Toward Percutaneous Aortic Valve Replacement." Circulation, 105: 775-778, Feb. 12, 2002.
Carpentier-Edwards PERIMOUNT Bioprosthesis (2003).
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcitic Aortic Stenosis: First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
Dake et al., "Transluminal Placement of Endovascular Stent-Grafts for the Treatment of Descending Thoracic Aortic Aneurysms." New Engl. J. of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Dotter, "Transluminally-Placed Coilspring Endarterial Tube Grafts," Investigative Radiology, pp. 329-332 (1969).
Emery et al., 'Replacement of the Aortic Valve in Patients Under 50 Years of Age: Long-Term Follow-Up of the St. Jude Medical Prosthesis.' Ann. Thorac. Surg., 75:1815-9 (2003).
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Fluency Vascular Stent Graft Instructions for Use (2003).
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).

* cited by examiner

REPLACEMENT HEART VALVE IMPLANT WITH INVERTIBLE LEAFLETS

RELATED APPLICATIONS

This application claims priority to U.S. Provisional Application Ser. No. 62/336,944, filed May 16, 2016.

TECHNICAL FIELD

The present disclosure pertains to medical devices, and methods for manufacturing and/or using medical devices. More particularly, the present disclosure pertains to configurations of a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a locking mechanism for a medical implant may comprise a buckle member, a post member axially translatable with respect to the buckle member, the post member including a receiving portion proximate a proximal end of the post member, a distal end, a laterally-arched central body portion extending between the receiving portion and the distal end, and a cantilevered leg extending proximally from the distal end, and an actuator element including a proximal shaft portion and a distal engagement portion, the distal engagement portion being configured to releasably engage the receiving portion of the post member. The proximal shaft portion may be pivotable with respect to the distal engagement portion.

In addition or alternatively, and in a second aspect, the actuator element includes a hinge element disposed between the proximal shaft portion and the distal engagement portion.

In addition or alternatively, and in a third aspect, the post member includes at least one aperture extending therethrough proximate the distal end, the at least one aperture being configured to receive a coupling element therethrough.

In addition or alternatively, and in a fourth aspect, the distal engagement portion includes a lateral protrusion proximate a distal end of the distal engagement portion.

In addition or alternatively, and in a fifth aspect, the lateral protrusion is configured to engage with an aperture disposed within the receiving portion.

In addition or alternatively, and in a sixth aspect, the laterally-arched central body portion includes a tooth extending laterally therefrom.

In addition or alternatively, and in a seventh aspect, the tooth extends toward the cantilevered leg.

In addition or alternatively, and in an eighth aspect, the central body portion arches laterally in a first direction relative to the proximal end and the distal end, and the tooth extends laterally in the first direction from the central body portion.

In addition or alternatively, and in a ninth aspect, the cantilevered leg includes a longitudinally-oriented slot extending therethrough.

In addition or alternatively, and in a tenth aspect, the receiving portion includes a first portion and a second portion configured to splay apart as the post member is translated proximally within the buckle member to release the distal engagement portion therefrom.

In addition or alternatively, and in an eleventh aspect, the buckle member is formed of a substantially rigid material.

In addition or alternatively, and in a twelfth aspect, the central body portion is configured to flex towards a substantially straight configuration upon proximal translation through the buckle member.

In addition or alternatively, and in a thirteenth aspect, a replacement heart valve implant may comprise a tubular anchor member defining a central longitudinal axis; a plurality of locking mechanisms, each locking mechanism comprising a buckle member fixedly attached to the tubular anchor member, and a post member axially translatable with respect to the buckle member, the post member including a receiving portion proximate a proximal end of the post member, a distal end, a laterally-arched central body portion extending between the receiving portion and the distal end, and a cantilevered leg extending proximally from the distal end; a plurality of valve leaflets, wherein each valve leaflet is coupled to the cantilevered leg of at least one of the plurality of locking mechanisms; and a plurality of actuator elements corresponding to the plurality of locking mechanisms, each actuator element including a proximal shaft portion and a distal engagement portion, wherein the proximal shaft portion is pivotable relative to the distal engagement portion, wherein the distal engagement portion is releasably fixed to the receiving portion of one post member.

In addition or alternatively, and in a fourteenth aspect, the buckle member of each locking mechanism is positioned against an inner surface of the tubular anchor member.

In addition or alternatively, and in a fifteenth aspect, the plurality of valve leaflets is configured to shift between an everted position wherein a free end of each of the plurality of valve leaflets is disposed distally of the tubular anchor member, and a deployed position wherein the free end of each of the plurality of valve leaflets is disposed within the tubular anchor member.

In addition or alternatively, and in a sixteenth aspect, in the everted position, each of the plurality of actuator elements extends distally of the tubular anchor member.

In addition or alternatively, and in a seventeenth aspect, each of the plurality of valve leaflets is secured to the tubular anchor member at a secured end opposite the free end.

In addition or alternatively, and in an eighteenth aspect, a replacement heart valve implant may comprise a tubular anchor member defining a central longitudinal axis, the tubular anchor member being configured to shift between a delivery configuration and a deployed configuration; a plurality of locking mechanisms, each locking mechanism comprising a buckle member fixedly attached to the tubular anchor member, and a post member axially translatable with respect to the buckle member, the post member including a receiving portion proximate a proximal end of the post member, a distal end, a laterally-arched central body portion extending from the receiving portion to the distal end, and a cantilevered leg extending proximally from the distal end; a plurality of valve leaflets, wherein each valve leaflet is coupled to the cantilevered leg of at least one of the plurality of locking mechanisms; and a plurality of actuator elements corresponding to the plurality of locking mechanisms, each actuator element including a proximal shaft portion pivotably connected to a distal engagement portion, the distal engagement portion being releasably fixed to the receiving portion of one post member, wherein the distal engagement portion is configured to pivot with respect to the proximal shaft portion in a radial direction relative to the central longitudinal axis.

In addition or alternatively, and in a nineteenth aspect, each actuator element extends through the buckle member of its corresponding locking mechanism when the tubular anchor member is in the delivery configuration, and each actuator element is configured to translate the post member of its corresponding locking mechanism into engagement with the buckle member of its corresponding locking mechanism upon proximal retraction of the plurality of actuator elements.

In addition or alternatively, and in a twentieth aspect, the post member is at least partially disposed distally of the tubular anchor member when the tubular anchor member is in the delivery configuration, and the post member is locked within the buckle member when the tubular anchor member is in the deployed configuration.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
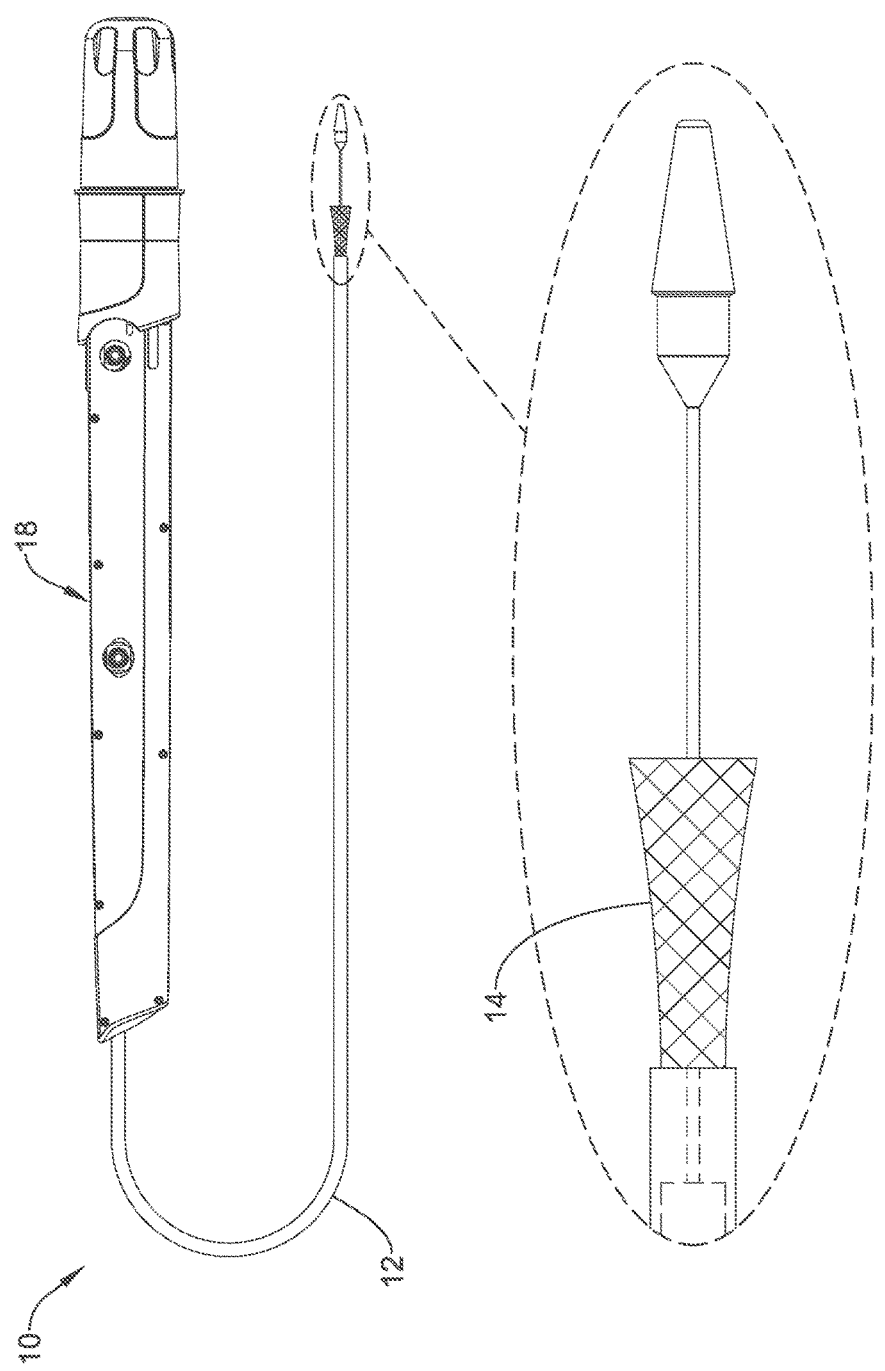
FIG. 1 illustrates an example medical implant system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical implant system 10, shown schematically in FIG. 1 for example. It should be noted that in any given figure, some features of the medical implant system 10 may not be shown, or may be shown schematically, for simplicity. Additional details regarding some of the components of the medical implant system 10 may be illustrated in other figures in greater detail. A medical implant system 10 may be used to deliver and/or deploy a variety of medical devices to a number of locations within the anatomy. In at least some embodiments, the medical implant system 10 may include a replacement heart valve delivery system (e.g., a replacement aortic valve delivery system) that can be used for percutaneous delivery of a medical implant 14, such as a replacement heart valve. This, however, is not intended to be limiting as the medical implant system 10 may also be used for other interventions including valve repair, valvuloplasty, and the like, or other similar interventions.

The medical implant system 10, as seen in FIG. 1 for example, may generally be described as a catheter system that includes a delivery system 12 and the medical implant 14 (e.g., a replacement heart valve implant, for example, which term may be used interchangeably with the term "medical implant" herein) which may be coupled to the delivery system 12 and disposed within a lumen of the delivery system 12 during delivery of the medical implant 14. In some embodiments, a handle 18 may be disposed and/or attached at a proximal end of the delivery system 12, as seen in FIG. 1, and may include at least one actuation means associated therewith. In some embodiments, the handle 18 may be configured to manipulate the position of the delivery system 12 and/or aid in the deployment of the medical implant 14. In some embodiments, the medical implant system 10 may include a nose cone disposed at a distal end of a guidewire extension tube, wherein the guidewire extension tube may extend distally from the delivery system 12. In at least some embodiments, the nose cone may be designed to have an atraumatic shape. In some embodiments, the nose cone may include a ridge or ledge that is configured to abut a distal tip of the delivery system 12 during delivery of the medical implant 14.

Figure 2:
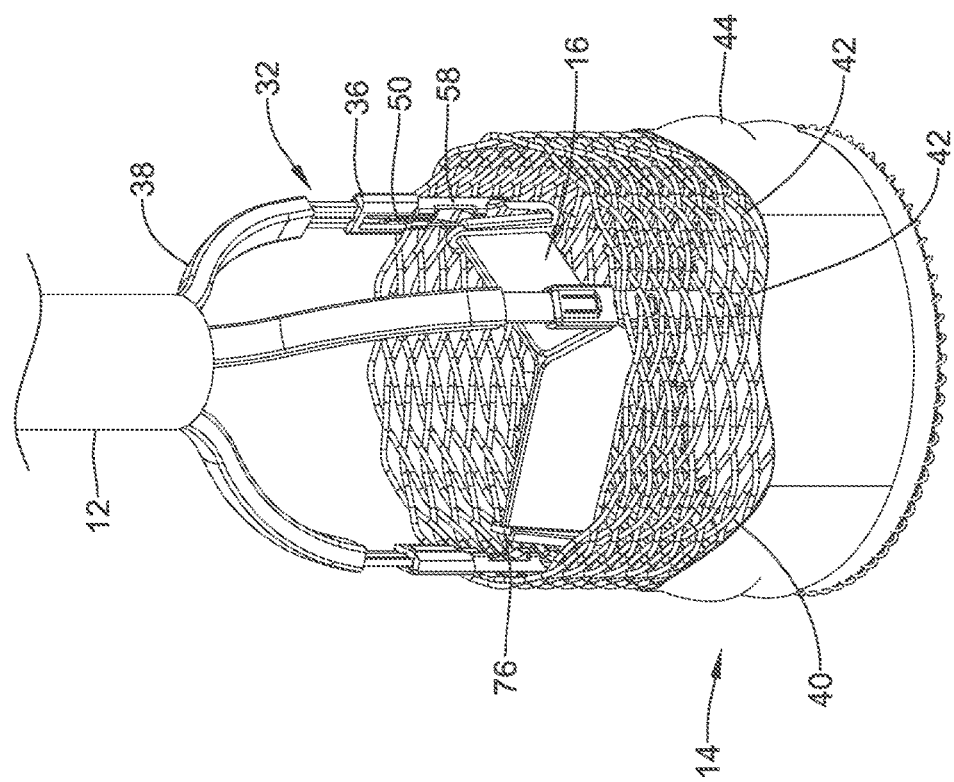
FIG. 2 illustrates an example medical implant in a deployed configuration.

In use, the medical implant system 10 may be advanced percutaneously through the vasculature to a position proximate to an area of interest and/or a treatment location. For example, in some embodiments, the medical implant system 10 may be advanced through the vasculature to a position proximate to a defective native valve (e.g., aortic valve, mitral valve, etc.). Alternative approaches to treat a defective aortic valve and/or other heart valve(s) are also contemplated with the medical implant system 10. During delivery, the medical implant 14 may be generally disposed in an elongated and low profile "delivery" configuration within the delivery system 12. Once positioned, at least a portion of the delivery system 12 may be retracted relative to the medical implant 14 to expose the medical implant 14. In some embodiments, the medical implant 14 may be disposed in an "everted" configuration while disposed within the lumen and/or the distal end of the delivery system 12 and/or immediately upon exposure after retracting the delivery system 12. In some embodiments, the "delivery" configuration and the "everted" configuration may be substantially similar and/or may be used interchangeably. The medical implant 14 may be actuated using the handle 18 in order to translate the medical implant 14 into a generally shortened and larger profile "deployed" configuration suitable for implantation within the anatomy, as seen in FIG. 2 for example. When the medical implant 14 is suitably deployed within the anatomy, the medical implant 14 may be released and/or detached from the medical implant system 10 and the delivery system 12 can be removed from the vasculature, thereby leaving the medical implant 14 in place in a "released" configuration, to function as, for example, a suitable replacement for the native valve. In at least some interventions, the medical implant 14 may be deployed within the native valve (e.g., the native valve is left in place and not excised). Alternatively, the native valve may be removed and the medical implant 14 may be deployed in its place as a replacement.

In some embodiments, the delivery system 12 may include at least one lumen extending therethrough. For example, in some embodiments, the delivery system 12 may include a first lumen, a second lumen, a third lumen, and a fourth lumen. Other configurations are also contemplated. In general, the at least one lumen extend along an entire length of the delivery system 12. Other embodiments are contemplated, however, where at least one of the at least one lumen extends along only a portion of the length of the delivery system 12. In some embodiments, a coupler assembly 32 may be attached at and/or to a distal end of the delivery system 12. In some embodiments, the coupler assembly 32 may releasably couple the medical implant 14 and/or selected components thereof to the delivery system 12. In some embodiments, the coupler assembly 32 may include a plurality of fingers, as discussed in more detail below.

In some embodiments, disposed within one of the lumens of the delivery system 12 may be at least one actuator member 50, which may be used to actuate (e.g., translate axially or longitudinally, and/or expand) the medical implant 14 between a delivery configuration and a deployed configuration. In some embodiments, the medical implant system 10 may include at least one actuator member 50. In some embodiments, the at least one actuator member 50 may include a plurality of actuator members 50, two actuator members 50, three actuator members 50, four actuator members 50, or another suitable or desired number of actuator members 50. For the purpose of illustration only, the medical implant system 10 and/or the medical implant 14 of FIG. 2 is configured to use three actuator members 50. In use, a proximal end of an actuator member 50 may be connected to the handle 18, and/or manipulated or otherwise actuated by a user using the handle 18, to shift the tubular anchor member 40 and/or the medical implant 14 from a "delivery" configuration to a "deployed" configuration, and later to a "released" configuration. During the release process for the medical implant 14, (e.g., as the medical implant 14 and/or the tubular anchor member 40 is actuated from the "delivery" configuration to the "deployed" configuration to the "released" configuration), the at least one actuator member 50 may be retracted, withdrawn, and/or translated proximally relative to delivery system 12, the medical implant 14, and/or components or elements thereof.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator member", "the locking element", "the lumen", or other features may be equally referred to all instances and quantities beyond one of said feature. As such, it will be understood that the following discussion may apply equally to any and/or all of the components for which there are more than one within the medical implant 14 (e.g., the at least one actuator member 50, the plurality of locking elements, etc.) and/or the medical implant system 10, unless explicitly stated to the contrary. Additionally, not all instances of some elements or features may be shown in each figure for clarity.

FIG. 2 illustrates some selected components of the medical implant system 10 and/or the medical implant 14 in the "deployed" configuration. For example, the medical implant 14 includes a plurality of valve leaflets 16 (e.g., bovine pericardial, polymeric, etc.) which may be secured to a tubular anchor member 40 that is actuatable between an elongated "delivery" configuration, as in FIG. 1 for example, and an expanded "deployed" configuration, as in FIG. 2. In some embodiments, the tubular anchor member 40 may include a proximal end and a distal end. In some embodiments, the tubular anchor member 40 may form a tubular structure defining a central longitudinal axis extending from the proximal end of the tubular anchor member 40 to the distal end of the tubular anchor member 40, and/or a lumen extending through the tubular anchor member 40 along, parallel to, coaxial with, and/or coincident with the central longitudinal axis. In some embodiments, the tubular anchor member 40 may be and/or include a braid formed from at least one filament or wire (e.g., a single filament or wire, two filaments or wires, etc.). Other configurations are also contemplated. Some suitable but non-limiting materials for the tubular anchor member 40, for example metallic materials or polymeric materials, are described below.

In some embodiments, the tubular anchor member 40 may include and/or form a plurality of anchor member intersection points 42 distributed around a circumference of the tubular anchor member 40. In some embodiments, the plurality of anchor member intersection points 42 may include two or more overlapping segments (e.g., a first segment, a second segment, a third segment, etc.) of the tubular anchor member 40 and/or the braid, filaments, wires, etc. thereof. In some embodiments, the two or more overlapping segments may be arranged in an alternating over-and-under pattern or arrangement. For example, at a first anchor member intersection point 42, a first segment may be disposed radially outward of a second segment. At an adjacent second anchor member intersection point 42 including the first segment, the first segment may be disposed radially inward of an overlapping segment (e.g., a third segment). If the first segment (or any single segment) is followed around the circumference of the tubular anchor member 40, the over-under-over pattern would continue alternating about the entire circumference of the tubular anchor member 40.

In some embodiments, the medical implant 14 may include a plurality of locking mechanisms attached to the tubular anchor member 40, the plurality of locking mechanisms being configured to secure the tubular anchor member 40 in the "deployed" and/or "released" configuration(s). In some embodiments, the medical implant 14 and/or the tubular anchor member 40 may be reversed and/or longitudinally extended back toward the "delivery" configuration at any point up until the plurality of locking mechanisms actually "locks" the medical implant 14 and/or the tubular anchor member in the "deployed" configuration. In some embodiments, the at least one actuator member 50 may be configured to engage with the plurality of locking mechanisms and actuate the tubular anchor member 40 and/or the medical implant 14 between the "delivery" configuration, the "deployed" configuration, and/or the "released" configuration. In some embodiments, one actuator member 50 may correspond to, engage with, and/or actuate one locking mechanism. In some embodiments, each actuator member 50 may extend through a guide 38 adjacent to and covering one of the plurality of fingers, as described herein, of the coupler assembly 32, and through a collar 36 coupling and/or locking the finger to one of the plurality of locking mechanisms. The guide 38 may be disposed over each of the fingers proximal of the collar 36 and may serve to keep the fingers of the coupler assembly 32 associated with the actuator members 50 extending adjacent to (and axially slidable relative to) the fingers of the coupler assembly 32. Other configurations are also contemplated. For example, in some embodiments, one actuator member 50 may correspond to, engage with, and/or actuate more than one locking mechanism.

For simplicity and clarity purposes, not all elements of the disclosed invention are necessarily shown in each figure. In some illustrative examples, only one of the fingers of the coupler assembly 32, only one of the plurality of actuator members 50, only one of the post members 76, only one of the buckle members 58, only one of the collars 36, etc. are shown and discussed (the whole medical implant 14 and/or the tubular anchor member 40 may not be shown to facilitate understanding of the locking mechanisms and/or other elements). However, it will be understood that the following discussion may apply equally to any and/or all of the components for which there are more than one within the medical implant 14 (e.g., each of the plurality of fingers 34, collars 36, guides 38, actuator members 50, buckle members 58, post members 76, etc.) and/or the medical implant system 10.

In some embodiments, the plurality of locking mechanisms may each comprise a buckle member 58 or other receiving element fixedly attached to the tubular anchor member 40 (e.g., along an inner surface of the tubular anchor member 40), and an axially movable post member 76, for example at the commissure portions of the valve leaflets 16 (a post member 76 may sometimes be referred to as a "commissure post", which may serve to secure the plurality of valve leaflets 16, or a post member 76 may be connected and/or attached to a commissure post). In some embodiments, the buckle member 58 or other receiving element may be configured to slidably receive at least a portion of the post member 76 therein to engage with the buckle member 58 and thereafter lock the tubular anchor member 40 and/or the medical implant 14 in the "deployed" and/or the "released" configuration(s). In some embodiments, each of the plurality of valve leaflets 16 may be secured to the tubular anchor member 40 at one post member 76. In some embodiments, each of the plurality of valve leaflets 16 may be secured to two adjacent post members 76 at opposing sides of the valve leaflet 16. In at least some embodiments, a medical implant 14 may include a plurality of post members 76 and a corresponding plurality of buckle members 58 (e.g., one post member 76 for each/one buckle member 58). Other configurations and correspondences are also contemplated. Some suitable but non-limiting materials for the buckle member(s) 58 and/or the post member(s) 76, for example metallic materials or polymeric materials, may be described below.

Positioned proximate to (e.g., aligned with) the plurality of post members 76 may be a corresponding plurality of buckle members 58, which may be secured and/or fixedly attached to the tubular anchor member 40 (e.g., along the interior of the tubular anchor member 40) with sutures, adhesives, or other suitable mechanisms. In some embodiments, the post member 76 may be axially translatable relative to the buckle member 58 generally parallel to the central longitudinal axis of the tubular anchor member 40 when the post member 76 is at least partially disposed within and/or engaged with the buckle member 58.

In some embodiments, one buckle member 58 may be fixedly attached to the tubular anchor member 40 proximate to each of the three post members 76 and/or proximate the proximal end of the tubular anchor member 40. Accordingly, in some embodiments, the tubular anchor member 40 may have a total of three buckle members 58 and three post members 76 attached thereto. Similarly, one actuator member 50 may be associated with each post member 76 and buckle member 58, for a total of three actuator members 50 in the illustrated example(s). Other embodiments are contemplated where fewer or more buckle members 58, post members 76, and/or actuator members 50 may be utilized.

In some embodiments, the medical implant 14 and/or the tubular anchor member may be attached, coupled, and/or connected to the delivery system 12 by a coupler assembly 32, as seen in FIG. 2 for example. The coupler assembly 32 may generally include a cylindrical base (not shown) that may be attached to and/or extending from a distal end of the delivery system 12 and/or a portion or component thereof. Projecting distally from the base is a plurality of fingers (e.g., two fingers, three fingers, four fingers, etc.) that are each configured to engage with the medical implant 14 at the buckle members 58 (for example, at a proximal end of the buckle members 58), with the plurality of actuator members 50 extending therethrough and engaging the post members 76. A collar 36 may be disposed about each of the fingers 34 of the coupler assembly 32 to further assist in coupling, engaging, attaching, and/or otherwise holding together the fingers 34 and the buckle members 58. Some suitable but non-limiting materials for the coupler assembly 32, the fingers 34, the collars 36, and/or the guides 38, for example metallic materials or polymeric materials, may be described below.

In some embodiments, the plurality of valve leaflets 16 may be secured to the tubular anchor member 40 at, proximate to, and/or using (at least in part) individual, corresponding post members 76. In some embodiments, the plurality of valve leaflets 16 may also be secured to the distal end of the tubular anchor member 40. In at least some embodiments, the distal end of the tubular anchor member 40 may be interchangeably described as the "inflow" end or the "upstream" end of the tubular anchor member 40 and/or the medical implant 14. In at least some embodiments, the proximal end of the tubular anchor member 40 may be interchangeably described as the "outflow" end or the "downstream" end of the tubular anchor member 40 and/or the medical implant 14.

As will be described in more detail below, the post member 76 may be secured, attached, coupled, and/or connected to the distal end and/or the inflow end of the tubular anchor member 40. Therefore, in some embodiments, when the post member 76 is pulled proximally to engage the buckle member 58, as will be described herein, the distal end and/or the inflow end of the tubular anchor member 40 is also pulled proximally relative to the buckle member 58, thereby transitioning from the "delivery" configuration and/or the "everted" configuration toward the "deployed" configuration. In some embodiments, the plurality of valve leaflets 16 may be coupled and/or secured (e.g., to the post member 76, to the tubular anchor member 40, and/or back to themselves) using at least one suture, thread, wire, filament, or other suitable element. In some embodiments, the plurality of valve leaflets 16 may be coupled and/or secured (e.g., to the post member 76, to the tubular anchor member 40, and/or back to themselves) using an adhesive, a bonding agent, or other suitable securing means. In some embodiments, the plurality of valve leaflets 16 may be coupled and/or secured (e.g., to the post member 76, to the tubular anchor member 40, and/or back to themselves) using a fabric strip, a textile, or other thin flexible material. In some embodiments, the plurality of valve leaflets 16 may not be directly attached to the tubular anchor member 40.

In some embodiments, a seal member 44 may be circumferentially disposed on and/or about a distal portion and/or an inflow portion of the tubular anchor member 40, as seen in FIG. 2 for example, and as the term suggests, may help to seal an exterior of the medical implant 14 and/or the tubular anchor member 40 within and/or against a target site or area of interest upon deployment (e.g., in the "deployed" configuration and/or the "released" configuration), thereby inhibiting or preventing leakage around the medical implant 14 and/or the tubular anchor member 40. In some embodiments, the seal member 44 may be disposed about and/or radially outward of an outside surface of the tubular anchor member 40. In some embodiments, the seal member 44 may be disposed around a perimeter and/or on or against an exterior or outer surface of the tubular anchor member 40. In some embodiments, the seal member 44 may be coupled and/or secured at the distal end and/or the inflow end of the tubular anchor member 40.

In some embodiments, the seal member 44 may include a plurality of layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other configurations and/or other suitable materials are also contemplated.

In some embodiments, the modulus of elasticity may vary and/or be different from layer to layer. In other embodiments, the elongation to break may vary and/or be different from layer to layer. In some embodiments, the seal member 44 may also include a reinforcement, a reinforcing layer, and/or at least one reinforcing member added to the polymeric material prior to curing. The reinforcement, the reinforcing layer, and/or the at least one reinforcing member may comprise a woven or nonwoven fabric and may be positioned within or between the various layers. In some embodiments, the reinforcement, the reinforcing layer, and/or the at least one reinforcing member may be positioned on a radially innermost surface or radially outermost surface of the seal member 44. In some embodiments, the reinforcement, the reinforcing layer, and/or the at least one reinforcing member may be generally aligned. In some embodiments, the reinforcement, the reinforcing layer, and/or the at least one reinforcing member may be randomly oriented and/or disposed on the seal member 44.

In some embodiments, a distal end of the seal member 44 may include a reinforcing band fixedly attached to the seal member 44 at and/or proximate the distal end and/or the inflow end of the tubular anchor member 40. In some embodiments, the reinforcing band may be integrally formed with, incorporated into, adhered to, and/or at least partially embedded within the seal member 44. In some embodiments, the reinforcing band may be formed from a woven or nonwoven fabric strip, a textile, or other thin flexible material. The reinforcing band may provide tear resistance in the vicinity of sutures, filaments, or other attachment elements associated with components or aspects of the medical implant 14. In some embodiments, the seal member 44 and/or the reinforcing band may extend longitudinally beyond the distal end and/or the inflow end of the tubular anchor member 40.

In some embodiments, the plurality of valve leaflets 16 may each define a secured end and a free end opposite the secured end, wherein the free ends of the plurality of valve leaflets 16 come together to define an outflow end of a valve disposed within the tubular anchor member 40 in the "deployed" configuration. In some embodiments, the secured end of each of the plurality of valve leaflets 16 may be directly attached to the seal member 44 and/or the reinforcing band at and/or proximate the distal end and/or the inflow end of the tubular anchor member 40. In some embodiments, the plurality of valve leaflets 16 may not be attached directly to the distal end and/or the inflow end of the tubular anchor member 40. In some embodiments, the plurality of valve leaflets 16 may be configured to shift between a deployed position wherein the outflow end of the valve is disposed within the tubular anchor member 40, and an everted position wherein the outflow end of the valve is disposed outside of, distal of, and/or upstream of the tubular anchor member 40.

Figure 3:
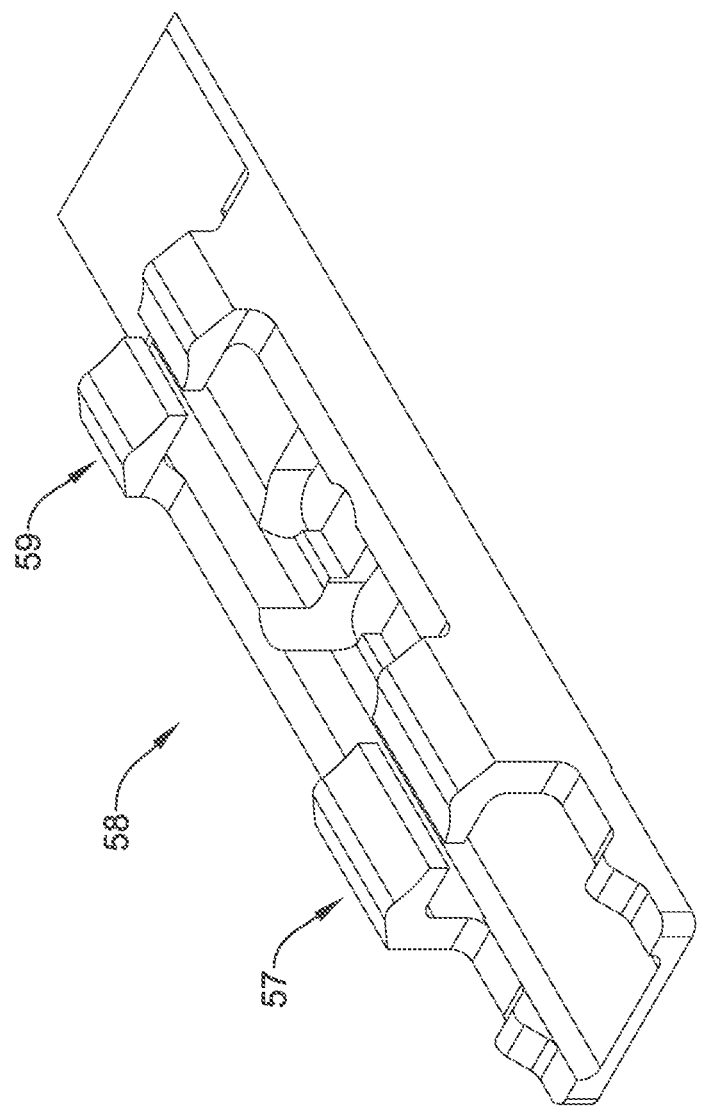
FIG. 3 is an isometric view of an example buckle member associated with an example medical implant.

As shown in FIG. 3, a buckle member 58 may include a proximal end and a distal end disposed opposite the proximal end. In some embodiments, the buckle member 58 may include a back wall extending from the proximal end to the distal end. In some embodiments, the buckle member 58 may include two axially-extending side walls extending radially inward toward the central longitudinal axis away from the back wall and/or the tubular anchor member 40, when the buckle member 58 is attached thereto. In some embodiments, the back wall may be configured to engage a radially inner surface of the tubular anchor member 40. In an example, the back wall may be configured to matingly engage the radially inner surface of the tubular anchor member 40 such that the back wall is disposed radially distant from the central longitudinal axis of the medical implant 14 relative to the two side walls. In some embodiments, the back wall may include a generally planar inner surface facing toward the central longitudinal axis when the buckle member 58 is fixedly attached and/or secured to the tubular anchor member 40. In some embodiments, the back wall may include a curved outer surface configured to mate with and/or lie against an inner surface of the tubular anchor member 40 when the buckle member 58 is fixedly attached and/or secured to the tubular anchor member 40.

In some embodiments, the two axially-extending side walls may include a first side wall and a second side wall. In some embodiments, each side wall may include a proximal upper flange 57 and a distal upper flange 59 spaced longitudinally apart from the proximal upper flange 57, the proximal upper flange 57 and the distal upper flange 59 each extending from a top of the side wall distant from the back wall, the proximal upper flange 57 and the distal upper flange 59 each extending inwardly toward a central plane through the buckle member 58 (and/or the central longitudinal axis) normal to the back wall and/or the generally planar inner surface. In at least some embodiments, the proximal upper flange 57 and the distal upper flange 59 each may be oriented generally parallel to the back wall and/or the generally planar inner surface of the back wall. In some embodiments, the distal upper flange(s) 59 may define a proximal locking face configured to engage a latch portion extending laterally from the post member 76, as described herein.

In some embodiments, the back wall may extend between the two side walls, such that the two side walls, the back wall, and/or the proximal upper flange(s) 57 and the distal upper flange(s) 59 define a channel extending axially through the buckle member 58. In some embodiments, the buckle member 58 and/or the channel may include a suitable shape and/or keying feature(s) configured to cooperate with the actuator member 50 and/or the post member 76 to prevent relative rotation between the actuator member 50 and/or the post member 76 and the buckle member 58. In some embodiments, the back wall may include at least one aperture disposed within the back wall and between the two side walls. In some embodiments, a fastening element (e.g., a suture, thread, wire, filament, etc.) may pass through the at least one aperture and secure the buckle member 58 to the tubular anchor member 40. In some embodiments, the back wall may include a recessed portion in communication with some or all of the at least one aperture of the buckle member 58.

In some embodiments, the buckle member 58 may be substantially rigid. In some embodiments, the buckle member 58 may be formed from a metallic material, a polymeric material, a ceramic material, a composite material, or other suitable materials or combinations thereof. In some embodiments, the buckle member 58 may be partially rigid and/or partially flexible. In some embodiments, a buckle member 58 may permit an actuator member 50 and/or a post member 76 to be slidably received within and/or axially translate through the channel. In some embodiments, the buckle member 58 may be configured to prevent the actuator member 50 and/or the post member 76 from exiting the buckle member 58 in a radially inward direction toward the central longitudinal axis of the tubular anchor member 40, thereby limiting motion of the actuator member 50 and/or the post member 76 within the tubular anchor member 40 to axial translation.

Figure 4:
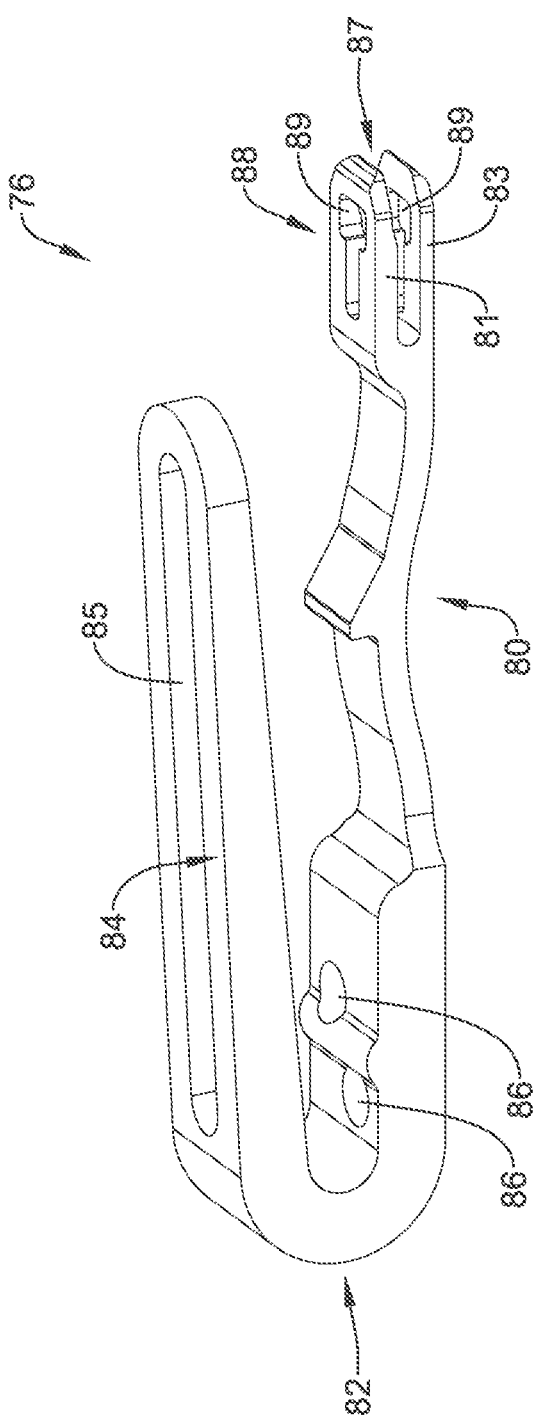
FIG. 4 is an isometric view of an example post member associated with an example medical implant.

As seen in FIG. 4, an example post member 76 may include a proximal end and a distal end, wherein the proximal end and the distal end may be defined based upon the orientation of the post member 76 when the medical implant 14 and/or the tubular anchor member 40 is in the "deployed" configuration and/or the "released" configuration. In some embodiments, the post member 76 may include a central body portion extending from the proximal end to the distal end, the central body portion being oriented generally along a first plane. In some embodiments, when the post member 76 is engaged with the buckle member 58, the central body portion may be oriented generally parallel to the generally planar inner surface of the back wall of the buckle member 58.

In some embodiments, the post member 76 may include a latch portion 80 connected to and/or integrally formed with or as a part of the central body portion. In some embodiments, the central body portion may be a laterally-arched central body portion extending laterally away from the first plane to form the latch portion 80. In some embodiments, the latch portion 80 may be resilient and/or self-biased away from the first plane. In some embodiments, the latch portion 80 may be configured to be deflected by the buckle member 58 and/or the distal upper flange(s) 59 as the post member 76 is translated proximally through the buckle member 58 and/or past the distal upper flange(s) 59.

In some embodiments, the post member 76 (in association and/or cooperation with axial translation of the actuator member 50) may be reversibly actuatable between a first orientation, wherein the proximal end extends distally from the central body portion (e.g., in the "delivery" and/or "everted" configuration), and a second orientation, wherein the proximal end extends proximally from the central body portion. In some embodiments, the post member 76 may be positioned and/or oriented in the second orientation in at least one configuration, including but not limited to, the "deployed" and/or "released" configurations. In some embodiments, the post member 76 may be axially translatable relative to the buckle member 58 and/or the tubular anchor member 40.

In some embodiments, the post member 76 may include a cantilevered leg 84 connected by a flexible hinge portion 82 at the distal end of the post member 76. In some embodiments, the cantilevered leg 84 may extend proximally from the hinge portion 82 and/or the distal end to a free end of the cantilevered leg 84 disposed radially inward from the central body portion and/or the latch portion 80 (relative to the tubular anchor member 40), when the post member 76 is in the second orientation. In some embodiments, the free end may be disposed proximal of the latch portion 80 when the post member 76 is in the second orientation. In some embodiments, the latch portion 80 may be disposed proximal of the distal end and/or the hinge portion 82 when the post member 76 is in the second orientation. In some embodiments, the cantilevered leg 84 may extend distally from the hinge portion 82 and/or the distal end to the free end of the cantilevered leg 84 disposed radially outward from the central body portion and/or the latch portion 80 (relative to the tubular anchor member 40), when the post member 76 is in the first orientation. In some embodiments, the free end may be disposed distal of the latch portion 80 when the post member 76 is in the first orientation. In some embodiments, the latch portion 80 may be disposed distal of the distal end and/or the hinge portion 82 when the post member 76 is in the first orientation.

In some embodiments, the hinge portion 82 may have and/or include a radius of curvature. For example, in some embodiments, the radius of curvature may be between 0 and 3 millimeters (mm). In some embodiments, the radius of curvature may be an inner radius of curvature of between 0 and 3 millimeters (mm). In some embodiments, the radius of curvature may be an outer radius of curvature of between 0 and 3 millimeters (mm). Other configurations and radii of curvature are also contemplated. In some embodiments, the hinge portion 82 may be configured to dispose the central body portion and the cantilevered leg 84 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion 82 flexibly attaches the cantilevered leg 84 to the central body portion of the post member 76. In some embodiments, at least part of the cantilevered leg 84 may longitudinally overlap the buckle member 58 along a central longitudinal axis of the tubular anchor member 40 in the "deployed" configuration.

In some embodiments, the cantilevered leg 84 may include a free end and a secured end, where the cantilevered leg 84 may be attached to the central body portion and/or the distal end of the post member 76 at the secured end of the cantilevered leg 84, which may connect directly to the hinge portion 82. In some embodiments, the free end of the cantilevered leg 84 may be unattached (e.g., not directly attached) to any other structure of the medical implant 14, except for the cantilevered leg 84 and/or the plurality of valve leaflets 16. In other words, in some embodiments, the free end of the cantilevered leg 84 may not be directly attached to any other structure or feature of the medical implant 14 (e.g., the buckle member 58, the tubular anchor member 40, etc.). In some embodiments, the distal end of the post member 76, which in at least some embodiments may be proximate to and/or include the hinge portion 82, may be coupled to the distal end of the tubular anchor member 40, such as, for example, by a fastening element such as a suture, a filament, a wire, or other suitable means, as described herein. In some embodiments, the central body portion may include at least one aperture or hole 86 configured to receive a coupling element therethrough for securing the post member 76 to a distal end of the tubular anchor member 40, such as the suture, for example. As such, when the post member 76 is pulled proximally to engage the buckle member 58, the distal end of the tubular anchor member 40 is also pulled proximally relative to the buckle member 58, thereby transitioning from the "delivery" configuration toward the "deployed" configuration.

In some embodiments, the cantilevered leg(s) 84 may include a first longitudinally-oriented slot 85 extending therethrough between the secured end of the cantilevered leg 84 and the free end of the cantilevered leg 84. In at least some embodiments, at least one of the plurality of valve leaflets 16 may be coupled to and/or attached to the cantilevered leg(s) 84. In some embodiments, at least one of the plurality of valve leaflets 16 extend through the first longitudinally-oriented slot 85 of the cantilevered leg(s) 84. In some embodiments, attachment of the plurality of valve leaflets 16 to the cantilevered leg(s) 84 may provide flexibility and/or a reduction in stress between the plurality of valve leaflets 16 and the tubular anchor member 40. In some embodiments, at least a portion of the plurality of valve leaflets 16 may axially or longitudinally overlap at least a portion of the buckle members 58 at a common position along a central longitudinal axis of the tubular anchor member 40, which in some embodiments may allow for a shorter overall length or height of the medical implant 14. In some embodiments, the plurality of valve leaflets 16 may be secured directly to the cantilevered leg(s) 84. In some embodiments, the plurality of valve leaflets 16 may not be directly secured to the central body portion of the post member 76, but is instead coupled to the post member 76 via the cantilevered leg(s) 84. In some embodiments, the plurality of valve leaflets 16 may be wrapped around at least a portion of the cantilevered leg(s) 84. In some embodiments, a distalmost end of the plurality of valve leaflets 16 may be coupled to the distal end of the tubular anchor member 40. In some embodiments, the plurality of valve leaflets 16 may be coupled and/or secured (e.g., to the cantilevered leg 84, to the tubular anchor member 40, and/or back to themselves) using at least one suture, thread, wire, filament, or other suitable element. In some embodiments, the plurality of valve leaflets 16 may be coupled and/or secured (e.g., to the cantilevered leg 84, to the tubular anchor member 40, and/or back to themselves) using an adhesive, a bonding agent, or other suitable securing means. In some embodiments, the plurality of valve leaflets 16 may be coupled and/or secured (e.g., to the cantilevered leg 84, to the tubular anchor member 40, and/or back to themselves) using a fabric, a textile, or other thin flexible material.

Figure 11:
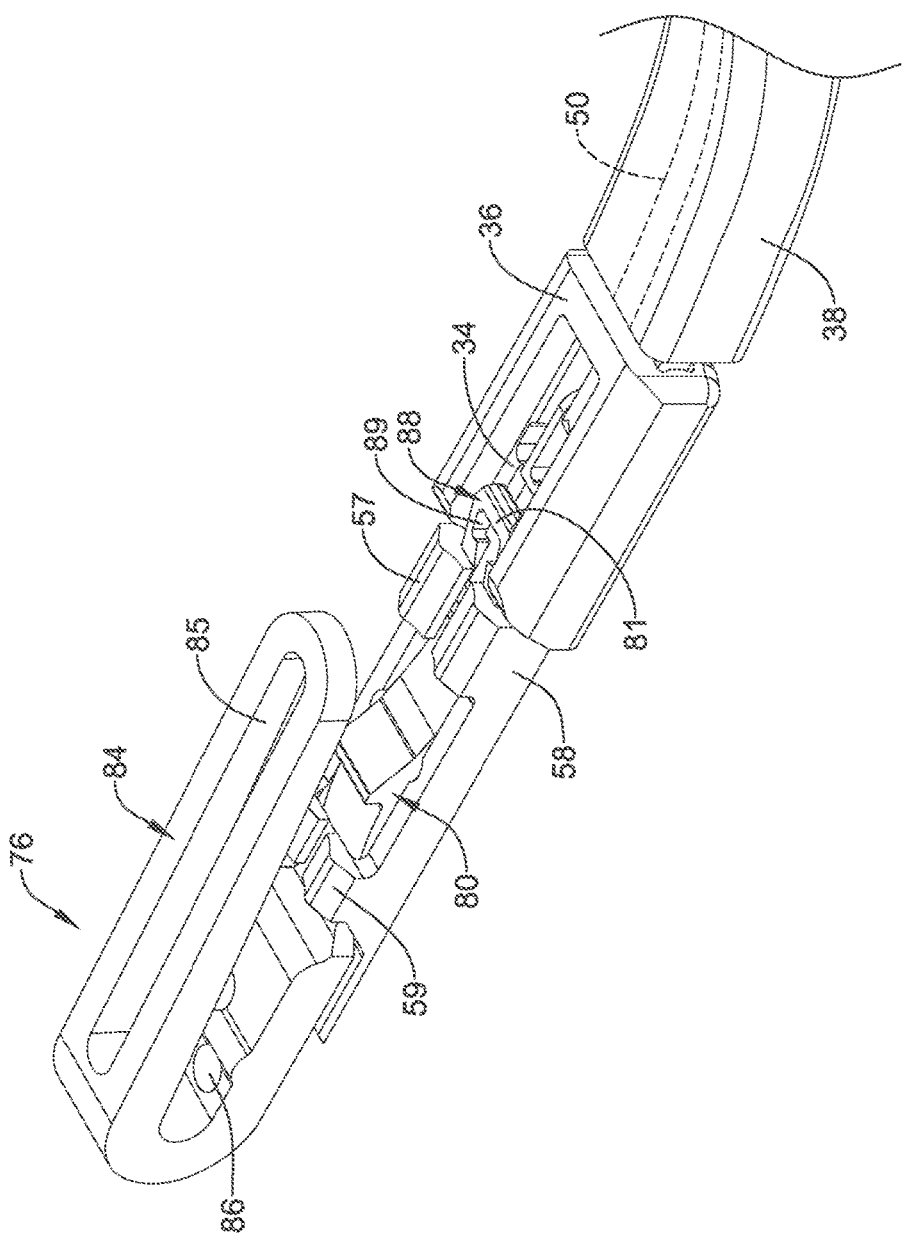
FIGS. 11-12 illustrate selected components of an example medical implant associated with an example medical implant system in a partially-released configuration.
Figure 12:
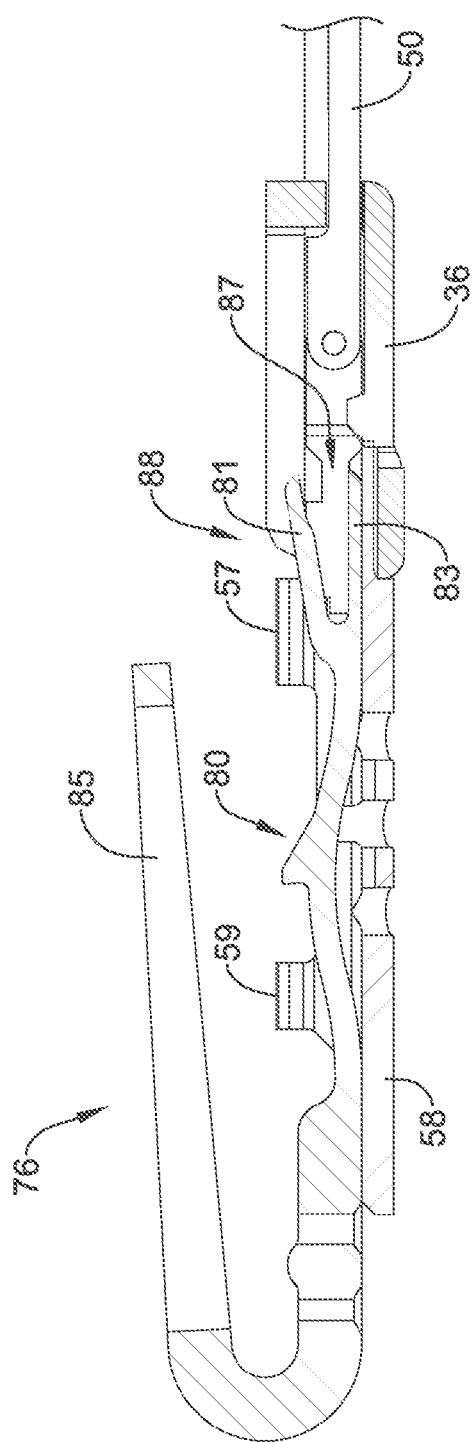

In some embodiments, the post member 76 may include a receiving portion 88 proximate the proximal end. In some embodiments, the receiving portion 88 may include a first portion 81 and a second portion 83, each extending proximally from the central body portion and/or the latch portion 80 when the post member 76 is in the second orientation. In some embodiments, the first portion 81 and the second portion 83 may be spaced apart by a second longitudinally-oriented slot 87 disposed therebetween. In some embodiments, the second longitudinally-oriented slot 87 may narrow distally when the post member 76 is in the second orientation. In some embodiments, each of the first portion 81 and the second portion 83 may include an aperture 89 extending into and/or from the second longitudinally-oriented slot 87 such that the aperture 89 of each respective portion is in communication with the second longitudinally-oriented slot 87. In some embodiments, the aperture 89 of the first portion 81 and/or the aperture 89 of the second portion 83 may extend partially through its respective portion in a radial (with respect to the central longitudinal axis and/or the tubular anchor member 40) direction. In some embodiments, the aperture 89 of the first portion 81 and/or the aperture 89 of the second portion 83 may extend completely through its respective portion in a radial (with respect to the central longitudinal axis and/or the tubular anchor member 40) direction. In some embodiments, the first portion 81 and the second portion 83 may be configured to releasably engage the actuator member 50, thereby releasably connecting the actuator member 50 to the proximal end of the post member 76. In some embodiments, as the actuator member 50 and/or the post member 76 is translated proximally through the buckle member 58 in the second orientation, the second longitudinally-oriented slot 87 of the post member 76 may contact and/or engage a distal end of the finger of the coupler assembly 32. In some embodiments, the distal end of the finger may be configured to splay apart the first portion 81 and the second portion 83 by forcing the first portion 81 radially inward toward the central longitudinal axis relative to, and/or away from, the second portion 83 as the post member 76 is translated proximally when the first portion 81 contacts the finger, as seen in FIGS. 11 and 12 for example.

In some embodiments, the latch portion 80 may be configured to engage the proximal locking face of the distal upper flange(s) 59 of the buckle member 58 when the post member 76 is in the second orientation, such that axial movement of the post member 76 distally relative to the buckle member 58 is prevented when the medical implant 14 and/or the tubular anchor member 40 is in the "deployed" configuration and/or the "released" configuration. In some embodiments, the latch portion 80 may include a transversely-oriented tooth extending laterally (or radially relative to the central longitudinal axis) therefrom and/or extends toward the cantilevered leg 84, wherein the tooth is configured to engage with the proximal locking face of the distal upper flange(s) 59 when the post member 76 is in the second orientation and/or the tubular anchor member 40 is in the "deployed" configuration and/or the "released" configuration. In some embodiments, the central body portion arches laterally (or radially relative to the central longitudinal axis) in a first direction relative to the proximal end and the distal end of the post member 76 (e.g., relative to the first plane), and the latch portion 80 and/or the tooth extends laterally (or radially relative to the central longitudinal axis) in the first direction from the central body portion.

In some embodiments, at least a portion of the post member 76 is flexible. In some embodiments, the latch portion 80 and/or the tooth may be movable relative to the central body portion. In some embodiments, the latch portion 80 may be deflectable relative to the central body portion such that the latch portion 80 and/or the tooth may translate laterally relative to the central body portion and/or radially outward relative to the central longitudinal axis. In some embodiments, the central body portion and/or the latch portion 80 may be configured to flex towards the first plane and/or a substantially straight configuration (e.g., radially relative to the central longitudinal axis) upon proximal translation of the post member 76 through the buckle member 58. In some embodiments, the free end of the cantilevered leg 84 may be movable toward and away from the central body portion (e.g., radially relative to the central longitudinal axis) by bending and/or pivoting the cantilevered leg 84 at and/or using the hinge portion 82.

In some embodiments, the central body portion may be unitary with and/or integrally formed with the latch portion 80, the hinge portion 82, the cantilevered leg 84, the receiving portion 88, and/or the first portion 81 and the second portion 83, of the post member 76 as and/or from a single piece of material. In some embodiments, the post member 76 may be formed from a single piece of wire, flat stock, or other suitable material as discussed herein. In some embodiments, the post member 76 may be formed by further processing the single piece of wire, flat stock, or other suitable material, such as by machining, stamping, laser cutting, or other suitable techniques.

Figure 5:
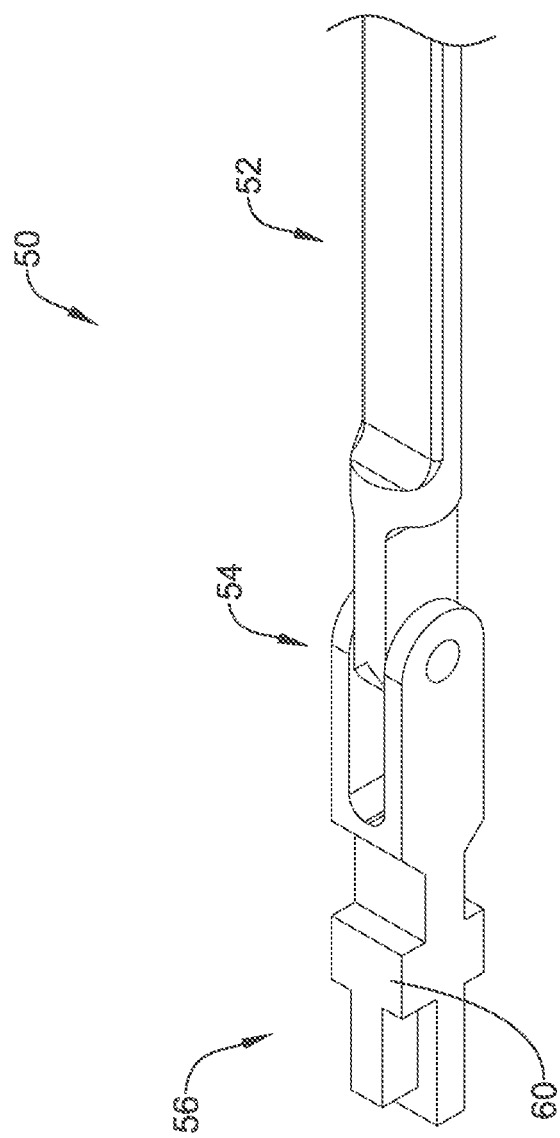
FIG. 5 is an isometric view of an example actuator member associated with an example medical implant system.

In some embodiments, an example actuator member 50, as seen in FIG. 5 for example, may include a proximal end and a distal end. In some embodiments, the actuator member 50 may include a proximal shaft portion 52 and a distal engagement portion 56 configured to be releasably engaged with and/or connected to the proximal end, the receiving portion 88, the first portion 81, and/or the second portion 83, of the post member 76. In some embodiments, the proximal shaft portion 52 may be pivotable with respect to the distal engagement portion 56. In some embodiments, the actuator member 50 may include a hinge element 54 disposed between the proximal shaft portion 52 and the distal engagement portion 56. In some embodiments, the hinge element 54 may include a pivot pin, or a plurality of pivot pins, fixedly attached to one of the proximal shaft portion 52 and the distal engagement portion 56, and a receiving element configured to pivotably engage the pivot pin, or the plurality of pivot pins, fixedly attached to the other one of the proximal shaft portion 52 and the distal engagement portion 56.

In some embodiments, the distal engagement portion 56 may include a lateral protrusion 60 proximate a distal end thereof. In some embodiments, the distal engagement portion 56 may include more than one lateral protrusion 60 proximate a distal end thereof. In some embodiments, the lateral protrusion 60 may be configured to matingly engage with the receiving portion 88, the aperture 89 of the first portion 81, and/or the aperture 89 of the second portion 83 of the post member 76. In some embodiments, the actuator member 50 may be prevented from rotating (e.g., is non-rotatable) relative to the post member 76 when the distal engagement portion 56 and/or the lateral protrusion 60 of the actuator member 50 is engaged with the receiving portion 88, the aperture 89 of the first portion 81, and/or the aperture 89 of the second portion 83 of the post member 76. In some embodiments, the actuator member 50 may be prevented from rotating (e.g., is non-rotatable) relative to the buckle member 58 when the distal engagement portion 56 and/or the lateral protrusion 60 of the actuator member 50 is engaged with the receiving portion 88, the aperture 89 of the first portion 81, and/or the aperture 89 of the second portion 83 of the post member 76, and/or when the post member 76 is engaged with the buckle member 58.

In use, the proximal end of the actuator member 50 may be connected to and/or manipulated or otherwise actuated by a user, for example using the handle 18, to shift the medical implant 14 from a "delivery" configuration and/or an "everted" configuration to a "deployed" configuration, and later to a "released" configuration. In some embodiments, the actuator member 50 may be axially translatable relative to the buckle member 58. In some embodiments, the actuator member 50 may extend through the channel of the buckle member 58 when the tubular anchor member 40 is in the "delivery" configuration and/or the "everted" configuration. In some embodiments, the actuator member 50 may extend distally of the tubular anchor member 40 in the "delivery" configuration and/or the "everted" configuration. In some embodiments, the actuator member 50 may be axially translatable within and/or through the channel of the buckle member 58 to engage the post member 76 with the buckle member 58.

In some embodiments, the actuator member 50 may be aligned with the post member 76 and/or the lateral protrusion(s) 60 may be releasably engaged with and/or connected to the proximal end of the post member 76 and/or the receiving portion 88, the aperture 89 of the first portion 81, and/or the aperture 89 of the second portion 83 of the post member 76. In some embodiments, the distal engagement portion 56 may be received within the second longitudinally-oriented slot 87 disposed between the first portion 81 and the second portion 83 of the post member 76. In some embodiments, the lateral protrusion(s) 60 may be configured to engage with, be received by, and/or extend into the aperture(s) 89 formed within each of the first portion 81 and the second portion 83 of the post member 76.

In some embodiments, the actuator member 50 and/or the proximal shaft portion 52 may be generally round, oblong, ovoid, rectangular, polygonal (e.g., two-sided, three-sided, four-sided, five-sided, six-sided, etc.) in shape. Other shapes, both regular and irregular, are also contemplated. For example, in some embodiments, the proximal shaft portion 52 may include a flattened portion or side oriented radially inward toward the central longitudinal axis. In some embodiments, the actuator member 50 may be formed from a single piece of wire, round stock, or other suitable material, as discussed herein. In some embodiments, the actuator member 50 may be formed by further processing the single piece of wire, round stock, or other suitable material, such as by machining, stamping, laser cutting, or other suitable techniques. Some suitable but non-limiting materials for the actuator member 50, the proximal shaft portion 52, the distal engagement portion 56, and/or the hinge element 54, for example metallic materials or polymeric materials, may be described below.

FIGS. 6-13 illustrate the general relationship and operation of selected components of a locking mechanism configured to lock the medical implant 14 (and/or the tubular anchor member 40) in the "deployed" configuration and/or the "released" configuration.

Figure 6:
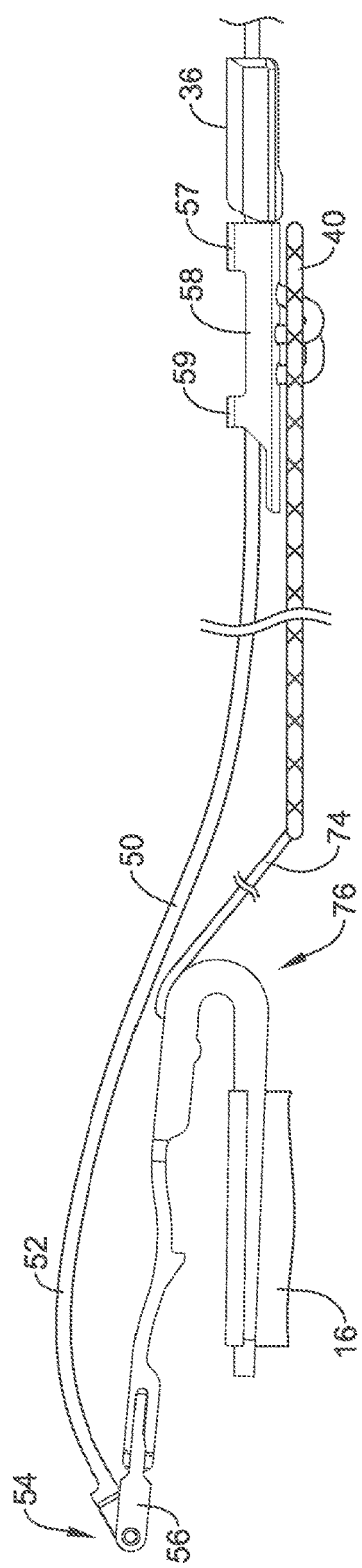
FIG. 6 illustrates selected portions of an example medical implant in a delivery or everted configuration.

During delivery, after the medical implant 14 is advanced within the anatomy to the desired and/or target location, at least a portion of the delivery system 12 may be withdrawn (e.g., moved proximally relative to the medical implant 14) to expose the medical implant 14 in the "delivery" configuration and/or the "everted" configuration. FIG. 6 illustrates selected elements of the medical implant system 10 in the "delivery" configuration and/or the "everted" configuration. In the "delivery" configuration and/or the "everted" configuration, the plurality of valve leaflets 16 may extend and/or be positioned distally of and/or away from the tubular anchor member 40. In some embodiments, in the "delivery" configuration and/or the "everted" configuration, the plurality of actuator members 50 may extend distally of, away from, and/or completely through the tubular anchor member 40, and/or the plurality of post members 76 may extend distally of and/or away from the tubular anchor member 40, as seen in FIG. 6 for example.

In some embodiments, a distal end of the axially movable post member 76 may be secured and/or attached (e.g., fixedly attached, movably attached, removably attached, etc.) to a distal portion of the tubular anchor member 40, such as by a suture 74, a tether, adhesives, or other suitable element. In some embodiments, the commissure post and/or the post member 76 may include at least one hole 86 (as seen in FIG. 4 for example) or other features provided to aid in securing and/or attaching the commissure post and/or the post member 76 to the tubular anchor member 40. For example, in some embodiments, the suture 74 may pass through the at least one hole 86 in the post member 76 and/or the suture 74 may be secured to the post member 76 using the at least one hole 86.

In some embodiments, the post member 76 may be movable relative to the tubular anchor member 40 and/or the buckle member 58. In some embodiments, the post member 76 may be axially or longitudinally movable relative to the tubular anchor member 40 and/or the buckle member 58. In some embodiments, the buckle member 58 may be fixedly attached to the tubular anchor member 40 at and/or proximate the proximal end thereof. Other embodiments are contemplated where the buckle member 58 may be movably or removably attached to the tubular anchor member 40. In some embodiments, the post member 76 may be movably or removably attached to the tubular anchor member 40 and the buckle member 58 may be movably or removably attached to the tubular anchor member 40. In some embodiments, the post member 76 may be secured or attached (e.g., fixedly attached, movably attached, removably attached, etc.) to a distal end of the tubular anchor member 40.

As seen in FIG. 6, when the medical implant 14 and/or the tubular anchor member is in the "delivery" configuration and/or the "everted" configuration, the distal engagement portion 56 of the actuator member 50 extends proximally from the hinge element 54 of the actuator member 50, and the post member 76 is in the first orientation. Similarly, when the medical implant 14 and/or the tubular anchor member 40 is in the "delivery" configuration and/or the "everted" configuration, the cantilevered leg 84 of the post member 76 extends radially outward from the hinge portion 82 and/or the central body portion. The plurality of valve leaflets 16 may be disposed distally of the tubular anchor member 40. In some embodiments, having the plurality of valve leaflets 16 and the plurality of post members 76 disposed outside of the tubular anchor member 40 may permit the tubular anchor member 40 to be collapsed to a smaller overall diameter and/or size for delivery due to less structure being disposed within the lumen of the tubular anchor member 40.

Figure 7:
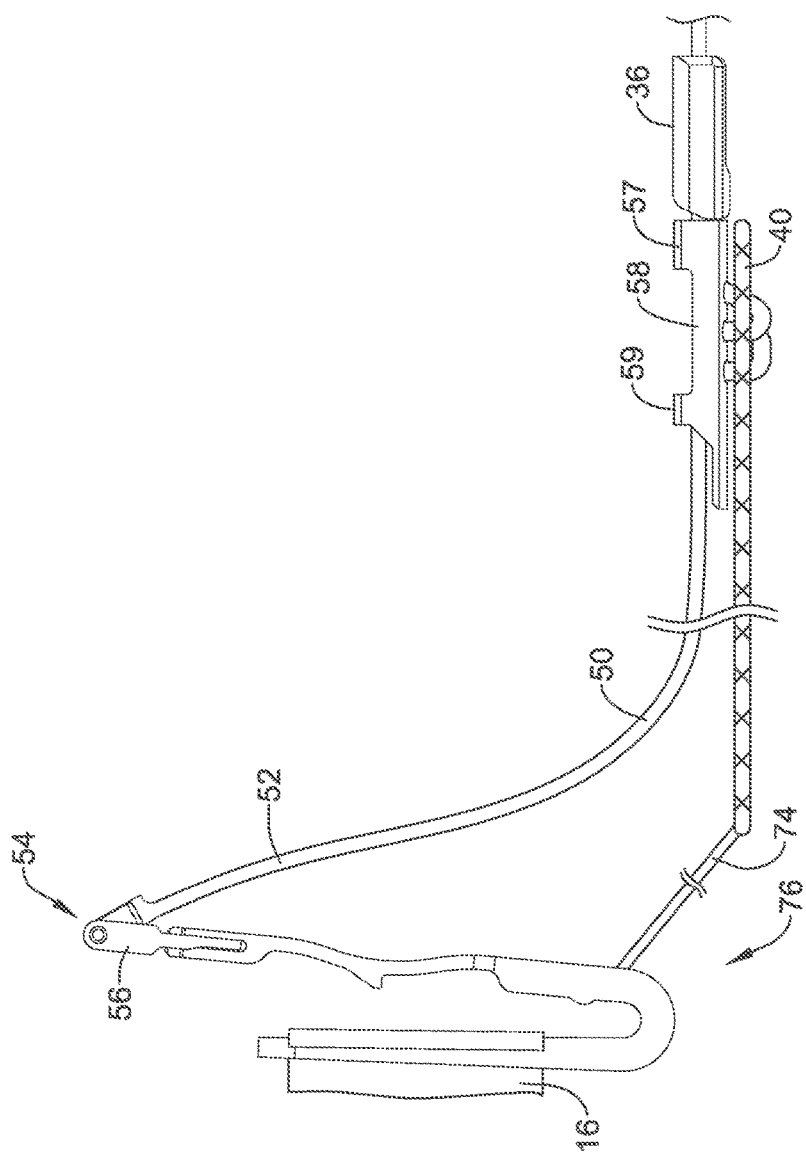
FIG. 7 illustrates selected portions of an example medical implant in a partially deployed configuration.

Turning now to FIG. 7, a user has manipulated and/or operated the handle 18 to partially withdraw the actuator member 50 through the buckle member 58, thereby drawing the post member 76 towards the buckle member 58. As may be seen in the figure, the post member 76 has begun to transition away from the first orientation and towards the second orientation. The medical implant 14 and/or the tubular anchor member 40 may thus be understood to be in a partially-everted configuration and/or a partially-deployed configuration. In the partially-everted configuration and/or the partially-deployed configuration, at least some portions of the post member 76 (e.g., the receiving portion, the first portion, the second portion, etc.) may extend radially inward toward the central longitudinal axis from the distal end of the post member 76. For example, the free end of the cantilevered leg 84 and/or the proximal end of the post member 76 may be positioned radially inward of the distal end of the post member 76 and/or the tubular anchor member 40.

Figure 8:
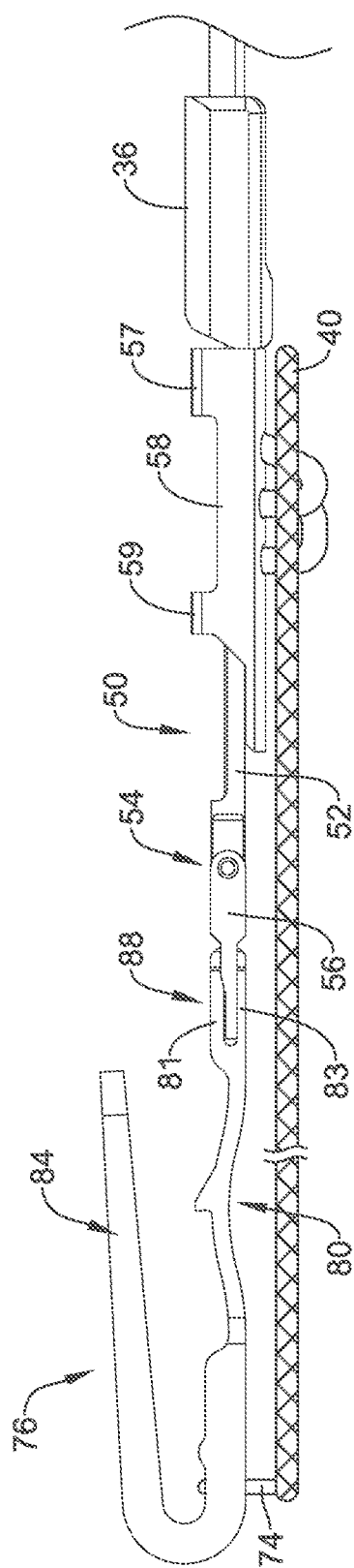
FIG. 8 illustrates selected portions of an example medical implant in a partially deployed configuration.

FIG. 8 illustrates selected components of the medical implant system 10 in a partially deployed configuration. Here it may be seen that the actuator member 50 has been retracted proximally, such that the distal engagement portion 56 has pivoted relative to the proximal shaft portion 52 at and/or about the hinge element 54 until the post member 76 is oriented in the second orientation to permit a smooth transition into the channel of the buckle member 58. In some embodiments, when the post member 76 is oriented in the second orientation, the proximal shaft portion 52 and the distal engagement portion 56 are coaxial with each other and/or the post member 76.

Figure 9:
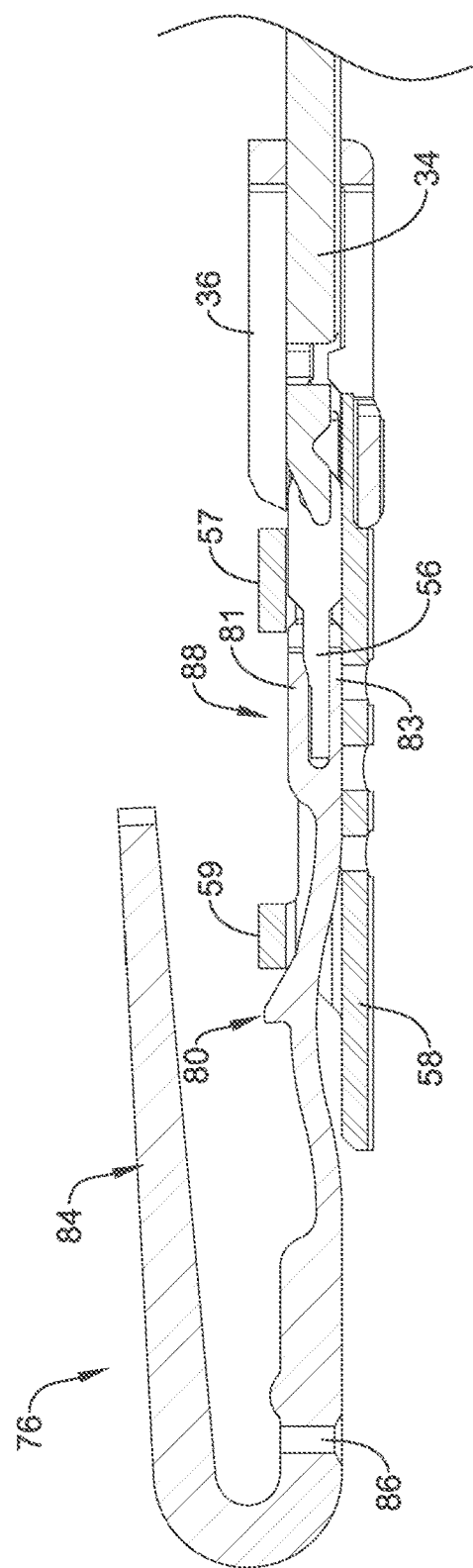
FIG. 9 illustrates selected components of an example medical implant associated with an example medical implant system in a partially deployed configuration.

FIG. 9 illustrates selected components in cross-section of the medical implant system 10 in a partially deployed configuration. As shown in the figure, as the actuator member 50 is translated proximally through the buckle member 58, the proximal end of the post member 76 may engage the buckle member 58 and be pulled into the channel thereof. As the latch portion 80 and/or the tooth approaches a distally facing surface of the distal upper flange(s) 59, the latch portion 80 and/or the tooth contacts the distally facing surface and the distally facing surface begins to interfere with proximal translation of the actuator member 50 and/or the post member 76. A user may notice and/or detect an increase in force as friction and/or interference between the latch portion 80 and/or the tooth and the distal upper flange(s) 59 of the buckle member 58 is generated. In some embodiments, a user may use this increase in force as a cue to re-assess the location and/or progress of the deployment, such as by a visualization means. If the placement is unsatisfactory, the user may reverse the direction of translation of the actuator member 50, and actuate the medical implant 14 and/or the tubular anchor member 40 toward the "delivery" configuration for repositioning and/or complete withdrawal, if necessary. If the placement is satisfactory, the user may continue using the handle 18 to translate the actuator member 50 and/or the post member 76 proximally until the latch portion 80 and/or the tooth has passed the distal upper flange(s) 59 of the buckle member 58, thereby placing the medical implant 14 and/or the tubular anchor member 40 in the "deployed" configuration, as seen in FIG. 10 for example.

Figure 10:
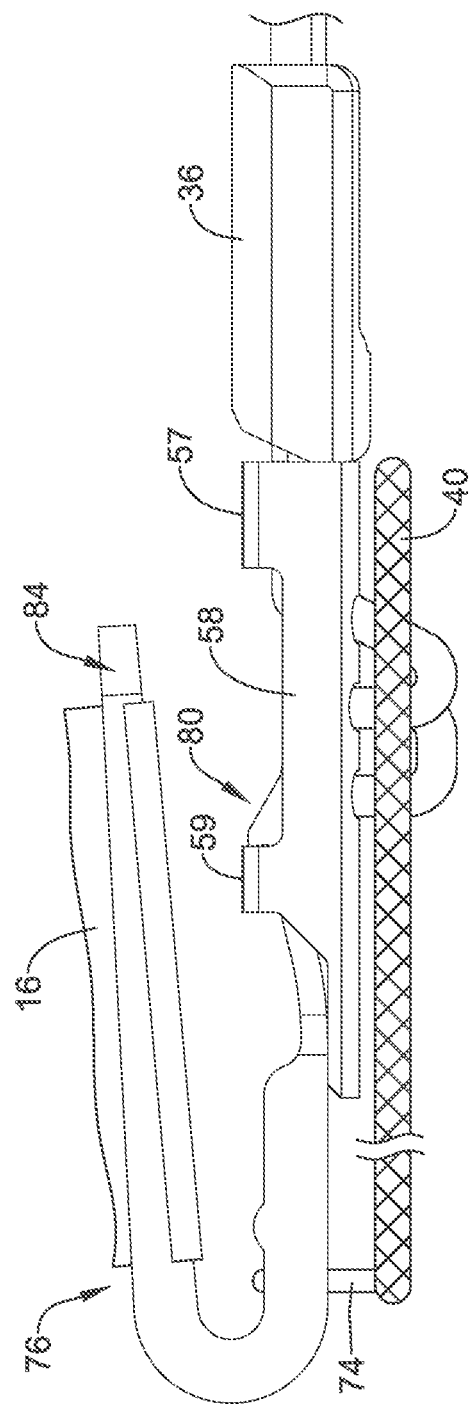
FIG. 10 illustrates selected components of an example medical implant associated with an example medical implant system in a deployed configuration.

FIG. 10 illustrates the proximal end of the post member 76 engaged with the buckle member 58 after further proximal retraction of the actuator member 50 through the buckle member 58. After the latch portion 80 and/or the tooth has passed the distal upper flange(s) 59 of the buckle member 58, contact between the latch portion 80 and/or the tooth and the proximally facing surface of the distal upper flange(s) 59 may prevent distal translation of the medical implant 14 and/or the tubular anchor member 40 toward the "delivery" configuration. In at least some embodiments, with the post member 76 engaged with the buckle member 58, the post member 76 may be positioned in the second orientation.

As seen in FIGS. 11 and 12, further proximal translation and/or retraction of the actuator member 50 relative to the buckle member 58 results in the receiving portion 88, and/or the first portion 81 and the second portion 83, of the post member 76 contacting and/or engaging a distal end of the finger 34. Continued proximal translation and/or retraction of the actuator member 50 may splay apart the receiving portion 88, and/or first portion 81 and the second portion 83, of the post member 76 as the distal end of the finger 34 extends into the second longitudinally-oriented slot 87, thereby disengaging the distal engagement portion 56 and/or the lateral protrusion(s) 60 of the actuator member 50 from the aperture(s) 89 in the receiving portion 88, and/or the aperture 89 in the first portion 81 and the aperture 89 in the second portion 83, of the post member 76.

Simultaneously with and/or immediately before splaying apart the receiving portion 88, and/or the first portion 81 and the second portion 83, of the post member 76 and/or disengagement of the distal engagement portion 56 and/or the lateral protrusion(s) 60 of the actuator member 50 from the aperture(s) 89 in the receiving portion 88, and/or the aperture 89 in the first portion 81 and the aperture 89 in the second portion 83, of the post member 76, a proximal face along a top or radially-inward facing side of the proximal shaft portion 52 of the actuator member 50 proximate to and/or proximal of the hinge element 54 may contact the collar 36, thereby proximally retracting the collar 36 along with the actuator member 50 to expose the finger 34 where it engages with the proximal end of the buckle member 58.

Figure 13:
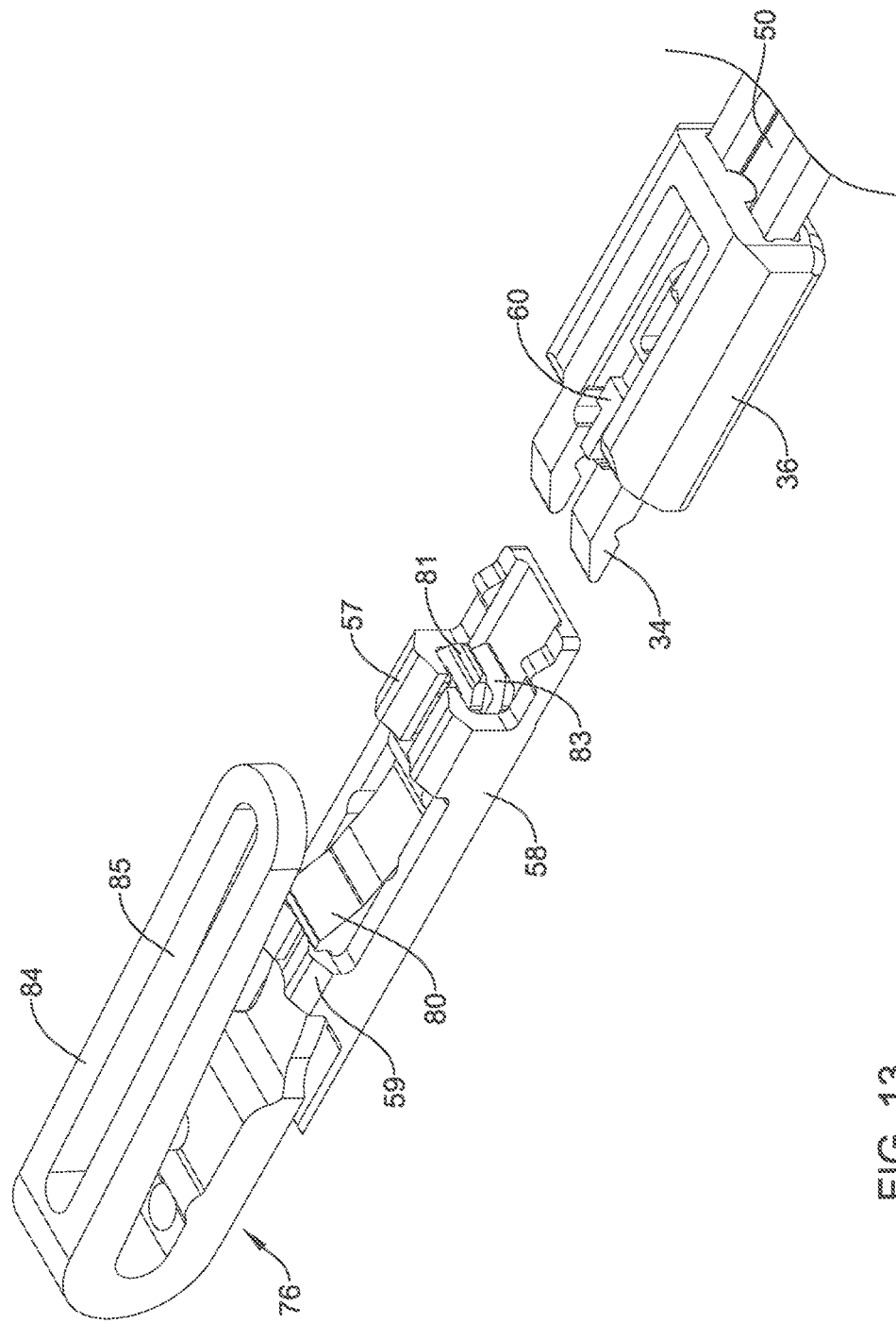
FIG. 13 illustrates selected components of an example medical implant associated with an example medical implant system in a released configuration.

In some embodiments, after disengaging the distal engagement portion 56 and/or the lateral protrusion(s) 60 of the actuator member 50 from the aperture(s) 89 in the receiving portion 88, and/or the aperture 89 in the first portion 81 and the aperture 89 in the second portion 83, of the post member 76, the medical implant 14 and/or the tubular anchor member 40 may experience a minor or slight "spring-back" toward the "delivery" configuration. Additionally, since the collar 36 is no longer maintaining the finger 34 and the buckle member 58 in a coupled relationship or configuration, the finger(s) 34 and/or the coupler assembly 32 may separate from the medical implant 14, the buckle member(s) 58, and/or the tubular anchor member 40. As noted above, the latch portion 80 and/or the tooth may contact the proximally facing surface of the distal upper flange(s) 59, preventing the medical implant 14 and/or the tubular anchor member 40 from actuating further toward the "delivery" configuration. Upon separation and/or disengagement of the coupler assembly 32 from the medical implant 14, the medical implant 14 and/or the tubular anchor member 40 may be left in the "released" configuration, as seen in FIG. 13 for example, and the delivery system 12 may be withdrawn from the patient.

The materials that can be used for the various components of the medical implant system 10 (and/or other systems disclosed herein) and the various elements thereof disclosed herein may include those commonly associated with medical devices. For simplicity purposes, the following discussion makes reference to the delivery system 12 and/or the medical implant 14. However, this is not intended to limit the devices and methods described herein, as the discussion may be applied to other elements, members, components, or devices disclosed herein, such as, but not limited to, the tubular anchor member 40, the actuator member 50, the locking mechanism, the post member 76, the buckle member 58, and/or elements or components thereof.

In some embodiments, the delivery system 12 and/or the medical implant 14, and/or components thereof (such as, but not limited to, the tubular anchor member 40, the locking mechanisms, the actuator members 50, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system 12 and/or the medical implant 14, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery system 12 and/or the medical implant 14. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery system 12 and/or the medical implant 14 to achieve the same result.

In some embodiments, a degree of Magnetic Resonance Imaging (MRI) compatibility is imparted into the medical implant 14. For example, the delivery system 12 and/or the medical implant 14, and/or components or portions thereof, may be made of a material that does not substantially distort the image and create substantial artifacts (e.g., gaps in the image). Certain ferromagnetic materials, for example, may not be suitable because they may create artifacts in an MRI image. The delivery system 12 and/or the medical implant 14, or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, a sheath or covering (not shown) may be disposed over portions or all of the delivery system 12 and/or the medical implant 14. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A locking mechanism for a medical implant, comprising:
    a buckle member;
    a post member axially translatable with respect to the buckle member, the post member including a receiving portion proximate a proximal end of the post member, a distal end, a laterally-arched central body portion extending between the receiving portion and the distal end, and a cantilevered leg extending proximally from the distal end; and
    an actuator element including a proximal shaft portion and a distal engagement portion, the distal engagement portion being configured to releasably engage the receiving portion of the post member;
    wherein the proximal shaft portion is pivotable with respect to the distal engagement portion.

2. The locking mechanism of claim 1, wherein the actuator element includes a hinge element disposed between the proximal shaft portion and the distal engagement portion.

3. The locking mechanism of claim 1, wherein the post member includes at least one aperture extending therethrough proximate the distal end, the at least one aperture being configured to receive a coupling element therethrough.

4. The locking mechanism of claim 1, wherein the distal engagement portion includes a lateral protrusion proximate a distal end of the distal engagement portion.

5. The locking mechanism of claim 4, wherein the lateral protrusion is configured to engage with an aperture disposed within the receiving portion.

6. The locking mechanism of claim 1, wherein the laterally-arched central body portion includes a tooth extending laterally therefrom.

7. The locking mechanism of claim 6, wherein the tooth extends toward the cantilevered leg.

8. The locking mechanism of claim 6, wherein the central body portion arches laterally in a first direction relative to the proximal end and the distal end, and the tooth extends laterally in the first direction from the central body portion.

9. The locking mechanism of claim 1, wherein the cantilevered leg includes a longitudinally-oriented slot extending therethrough.

10. The locking mechanism of claim 1, wherein the receiving portion includes a first portion and a second portion configured to splay apart as the post member is translated proximally within the buckle member to release the distal engagement portion therefrom.

11. The locking mechanism of claim 1, wherein the buckle member is formed of a substantially rigid material.

12. The locking mechanism of claim 1, wherein the central body portion is configured to flex towards a substantially straight configuration upon proximal translation through the buckle member.

13. A replacement heart valve implant, comprising:
a tubular anchor member defining a central longitudinal axis;
a plurality of locking mechanisms, each locking mechanism comprising:
a buckle member fixedly attached to the tubular anchor member; and
a post member axially translatable with respect to the buckle member, the post member including a receiving portion proximate a proximal end of the post member, a distal end, a laterally-arched central body portion extending between the receiving portion and the distal end, and a cantilevered leg extending proximally from the distal end;
a plurality of valve leaflets, wherein each valve leaflet is coupled to the cantilevered leg of at least one of the plurality of locking mechanisms; and
a plurality of actuator elements corresponding to the plurality of locking mechanisms, each actuator element including a proximal shaft portion and a distal engagement portion, wherein the proximal shaft portion is pivotable relative to the distal engagement portion, wherein the distal engagement portion is releasably fixed to the receiving portion of one post member.

14. The replacement heart valve implant of claim 13, wherein the buckle member of each locking mechanism is positioned against an inner surface of the tubular anchor member.

15. The replacement heart valve implant of claim 13, wherein the plurality of valve leaflets is configured to shift between an everted position wherein a free end of each of the plurality of valve leaflets is disposed distally of the tubular anchor member, and a deployed position wherein the free end of each of the plurality of valve leaflets is disposed within the tubular anchor member.

16. The replacement heart valve implant of claim 15, wherein in the everted position, each of the plurality of actuator elements extends distally of the tubular anchor member.

17. The replacement heart valve implant of claim 15, wherein each of the plurality of valve leaflets is secured to the tubular anchor member at a secured end opposite the free end.

18. A replacement heart valve implant, comprising:
a tubular anchor member defining a central longitudinal axis, the tubular anchor member being configured to shift between a delivery configuration and a deployed configuration;
a plurality of locking mechanisms, each locking mechanism comprising:
a buckle member fixedly attached to the tubular anchor member; and
a post member axially translatable with respect to the buckle member, the post member including a receiving portion proximate a proximal end of the post member, a distal end, a laterally-arched central body portion extending from the receiving portion to the distal end, and a cantilevered leg extending proximally from the distal end;
a plurality of valve leaflets, wherein each valve leaflet is coupled to the cantilevered leg of at least one of the plurality of locking mechanisms, and
a plurality of actuator elements corresponding to the plurality of locking mechanisms, each actuator element including a proximal shaft portion pivotably connected to a distal engagement portion, the distal engagement portion being releasably fixed to the receiving portion of one post member, wherein the distal engagement portion is configured to pivot with respect to the proximal shaft portion in a radial direction relative to the central longitudinal axis.

19. The replacement heart valve implant of claim 18, wherein each actuator element extends through the buckle member of its corresponding locking mechanism when the tubular anchor member is in the delivery configuration, and each actuator element is configured to translate the post member of its corresponding locking mechanism into engagement with the buckle member of its corresponding locking mechanism upon proximal retraction of the plurality of actuator elements.

20. The replacement heart valve implant of claim 18, wherein the post member is at least partially disposed distally of the tubular anchor member when the tubular anchor member is in the delivery configuration, and the post member is locked within the buckle member when the tubular anchor member is in the deployed configuration.

* * * * *